US008258345B2

(12) United States Patent
Casalnuovo

(10) Patent No.: US 8,258,345 B2
(45) Date of Patent: Sep. 4, 2012

(54) HYDROXYLATION OF β-DICARBONYLS WITH ZIRCONIUM CATALYSTS

(75) Inventor: Albert Loren Casalnuovo, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/048,999

(22) Filed: Mar. 16, 2011

(65) Prior Publication Data

US 2011/0196175 A1 Aug. 11, 2011

Related U.S. Application Data

(62) Division of application No. 12/748,745, filed on Mar. 29, 2010, now Pat. No. 7,939,685, which is a division of application No. 12/144,933, filed on Jun. 24, 2008, which is a division of application No. 10/476,916, filed as application No. PCT/US02/17755 on Jun. 6, 2002.

(60) Provisional application No. 60/302,148, filed on Jun. 29, 2001, provisional application No. 60/336,229, filed on Oct. 29, 2001.

(51) Int. Cl.
C07C 211/01 (2006.01)
(52) U.S. Cl. .......................................... 564/415; 556/56
(58) Field of Classification Search .................. 564/415
See application file for complete search history.

(56) References Cited

U.S. PATENT DOCUMENTS 5,869,657 A 2/1999 Annis et al.

FOREIGN PATENT DOCUMENTS

| WO | WO92/11249 | 7/1992 |
| WO | WO93/19045 | 9/1993 |
| WO | WO95/29171 | 11/1995 |
| WO | WO96/31467 | 10/1996 |
| WO | WO98/05656 | 2/1998 |

OTHER PUBLICATIONS

Boettcher et al. Acta Chemica Scandinavica (1994), 48(12), 967-80.*
Subramanian et al. Inorganic Chemistry (1984), 23(17), 2564-72.*
Balsells et al. Inorganic Chemistry (2001), 40(22), 5568-5574.*
Tshuva et al. Tetrahedron Letters (2001), 42(36), 6405-6407.*
XP002211305—Xavier Baucherel et al., "Monhydroxylation of cyclic and acyclic beta-keto esters with molecular oxygen catalyzed by cobalt (II) chloride in neutral conditions" Tetrahedron Letters, vol. 41, 2000, pp. 1385-1387.
XP002211306—Edit Y. Tshuva et al., "Isospecific living polymerization of 1-hexene by a readily available nonmetallocene C2-symmetrical zirconium catalyst" J. Am. Chem. Soc., vol. 122, 2000, pp. 10706-10707.
XP002211307—Matthew B. Francis et al., "Discovery of novel catalysts for alkene epoxidation from metal-binding combinatorial libraries" Angew. Chem. Int. Ed., vol. 38, No. 7, 1999, pp. 937-941.

XP001094077—Pramod K. Singh et al., "Synthesis and in vitro trypanocidal activity of some novel iron chelating agents" Arzneim.-Forsch., vol. 47, No. 3, 1997, pp. 311-315.
XP002211308—Jaume Balsells et al, "Achiral tetrahydrosalen ligands for the synthesis of C2-symmetric titanium complexes: a structure and diastereoselectivity study" Inorg. Chem., vol. 40, 2001, pp. 5568-5574.
XP001096192—Horst Elias et al, "A dioxomolybdenum (VI) complex with a new enantiomerically pure tetrahydrosalen ligand" ACTA Cryst. C, vol. 53, 1997, pp. 862-864.
XP001096478—A. Bottcher et al., "A novel synthetic approach to Asymmetric Salen, Dihydrosalen and Tetrasalen Ligands: structures and 02-activating properties of their Ni (II) and Co(II) complexes" Zeitschrift Fur Naturforschung B, vol. 49, No. 8, 1994, pp. 1089-1100.

(Continued)

Primary Examiner — Kahsay T Habte
(74) Attorney, Agent, or Firm — Craig L. Hillemann

(57) ABSTRACT

The present invention pertains to a process for preparing a compound of Formula I that is achiral, racemic or enantiomerically enriched at the hydroxylation center indicated by *

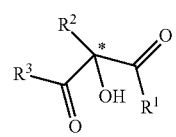

I comprising contacting a compound of Formula II

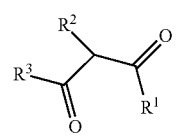

II with an oxidant selected from oxygen, hydrogen peroxide, peracids or alkyl hydroperoxides in the presence of a zirconium complex, wherein $R^1$, $R^2$ and $R^3$ are as defined in the disclosure. This invention also pertains to zirconium complexes useful in this procedure comprising zirconium and a ligand of Formula III or its enantiomer

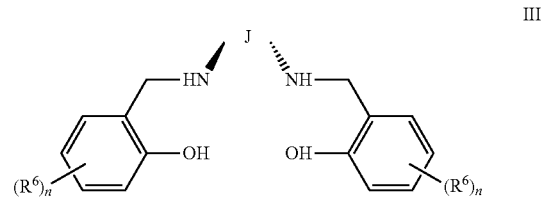

III wherein J, $R^6$ and n are as defined in the disclosure. This invention further pertains to a compound of Formula III or its enantiomer.

8 Claims, No Drawings

OTHER PUBLICATIONS

A. Boettcher et al., "Synthesis, structure and magnetic . . . ", *Acta Chem. Scand.* 1994, 48(12), 981-8.

A. Boettcher et al., "Syntheses, structures and magnetic . . . ", *Acta Chem. Scand.* 1994, 48(12), 967-80.

R. Shapiro et al., "Toward the Manufacture of Indoxacarb", Chapter 17 in *Synthesis and Chemistry of Agrochemicals VI*, D. R. Baker et. al. Eds, 2002, American Chemical Society, Washington, DC, pp. 178-185.

S. Vyskočil et al., "Synthesis of $C_2$-Symmetrical . . . ", *Collect. Czech. Chem. Commun.* 2000, 65, 539-548.

C. V. Ward et al., "New chiral catalysts for phospho-transfer", *Tetrahedron Lett.* 2000, 41, 6181-6184.

E. Y. Tshuva et al., "Single-step synthesis of salans . . . ", *Tetrahedron Lett.* 2001, 42(36), 6405-6407.

J. P. Duxbury et al., "Phospho-Aldol Catalysis via . . . ", *Organometallics* 2000, 19, 4445-4457.

Aldrich, Catalog Handbook of Fine Chemicals, 1998-1999, p. 1749.

Cotton & Wilkinson, Advanced Inorganic Chemistry, A Comprehensive Test, Third Edition (Interscience, New York, 1972), pp. 528-530.

H. Kanatomi, Bull. Chem. Soc. Japan 1983, 56, 99-104.

P. Woodman et al., Chem. Commun. 1996, 2735-2736.

\* cited by examiner

HYDROXYLATION OF β-DICARBONYLS WITH ZIRCONIUM CATALYSTS

FIELD OF THE INVENTION

The present invention pertains to a process for the hydroxylation of β-dicarbonyl compounds.

BACKGROUND OF THE INVENTION

Certain β-dicarbonyl compounds (i.e. β-keto esters and their hydroxylated derivatives) are useful as intermediates for the preparation of fine chemicals, pharmaceuticals and plant protection products such as arthropodicidal oxadiazines. Arthropodicidal oxadiazines are disclosed in PCT Publications WO 92/11249 and WO 93/19045. Methods of preparing these compounds have also been reported in WO 95/29171, including a preparative step involving the hydroxylation of β-keto esters. However, improved preparative methods for these compounds are desirable for more economic commercial operation. Accordingly, the present invention provides an improved process to prepare hydroxylated β-dicarbonyl compounds, including those useful in preparing arthropodicidal oxadiazines.

SUMMARY OF THE INVENTION

The present invention pertains to a process for preparing a compound of Formula I that is achiral, racemic or enantiomerically enriched at the hydroxylation center indicated by *

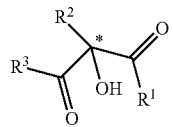

I wherein
- $R^1$ is H; or alkoxy, alkyl, cycloalkyl, cycloalkoxy, a phenyl ring, a phenoxy ring or a 5- or 6-membered heteroaromatic ring, each optionally substituted;
- $R^2$ is H; or alkyl, cycloalkyl, a phenyl ring, or a 5- or 6-membered heteroaromatic ring, each optionally substituted;
- $R^3$ is H; or alkoxy, alkyl, cycloalkyl, cycloalkoxy, a phenyl ring, a phenoxy ring or a 5- or 6-membered heteroaromatic ring, each optionally substituted; or
- $R^2$ and $R^3$ can be taken together to form an optionally substituted linking chain of 3 to 6 members including at least one carbon member, optionally including no more than two carbon members as C(=O), optionally including one member selected from nitrogen and oxygen, and optionally fused to a phenyl ring or a 5- or 6-membered heteroaromatic ring, each ring optionally substituted; or
- $R^1$ and $R^3$ can be taken together to form an optionally substituted linking chain of 2 to 5 members including at least one carbon member, optionally including no more than one carbon member as C(=O), and optionally fused to a phenyl ring or a 5- or 6-membered heteroaromatic ring, each ring optionally substituted;

comprising:
contacting a compound of Formula II

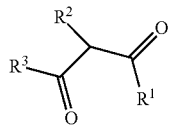

II wherein $R^1$, $R^2$ and $R^3$ are as defined above,
with a zirconium complex and an oxidant.

This invention also pertains to a chiral zirconium complex comprising zirconium and a chiral ligand of Formula III

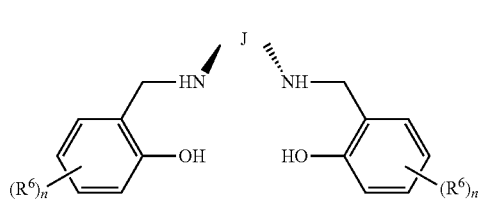

III wherein
- J is an optionally substituted linking chain of 2 to 4 members consisting of at least one carbon atom member and optionally one member selected from nitrogen and oxygen, of which no more than two carbon atom members are substituted as C(=O); the linking chain optionally fused through adjacent linking chain members to 1 or 2 rings or ring systems selected from the group consisting of a $C_3$-$C_8$ cycloalkyl ring, a $C_3$-$C_8$ nonaromatic heterocyclic ring, a phenyl ring or a 1,2-naphthalenyl ring system, each ring or ring system optionally substituted; such that the attached nitrogen atoms are held in a stereospecific orientation with respect to J and each other as depicted;
- each $R^6$ is independently selected from the group consisting of halogen; $NO_2$; cyano; $C_2$-$C_5$ alkoxycarbonyl; $N(C_1$-$C_4$ alkyl$)_2$; $CON(C_1$-$C_4$ alkyl$)_2$; $C_1$-$C_4$ alkoxy; $C_2$-$C_5$ alkylcarbonyloxy; $C_2$-$C_5$ alkoxycarbonyloxy; optionally substituted phenylcarbonyloxy; tri($C_1$-$C_4$ alkyl)silyl; tri($C_1$-$C_4$ alkyl)siloxy; $C_1$-$C_4$ alkyl optionally substituted with 1-3 phenyl rings; $C_3$-$C_6$ cycloalkyl optionally substituted with $C_1$-$C_2$ alkyl; adamantyl; a phenyl ring, or a 5- or 6-membered heteroaromatic ring, each ring optionally substituted; and
- when two $R^6$ are attached to adjacent phenyl ring carbon atoms, said two $R^6$ may be taken together with the phenyl ring to form a naphthalene ring system optionally substituted on either ring of said naphthalene ring system; and
- each n is independently an integer from 0 to 4.

This invention also pertains to a chiral zirconium complex comprising zirconium and a ligand that is the enantiomer of Formula III, said enantiomer designated Formula ent-III.

This invention also pertains to a compound of Formula III as defined above, provided that (a) when J is a $C_6$ cycloalkyl ring connected via adjacent carbon atoms to the remainder of Formula III, then at least one n is an integer from 1 to 4; (b) when J is a $C_6$ cycloalkyl ring connected via adjacent carbon atoms to the remainder of Formula III, on one phenyl ring n is 2 and $(R^6)_n$ is 3-t-butyl-5-methyl, then $(R^6)_n$ on the other phenyl ring is other than 3-t-butyl-5-methyl; and (c) when J is a 1,1'-binaphthalenyl ring system connected via the 2 and 2' positions to the remainder of Formula III, then at least one n is an integer from 1 to 4.

This invention also pertains to the enantiomer of the compound of Formula III (designated Formula ent-III), provided that (a) when J is a $C_6$ cycloalkyl ring connected via adjacent carbon atoms to the remainder of Formula ent-III, then at least one n is an integer from 1 to 4; (b) when J is a $C_6$ cycloalkyl ring connected via adjacent carbon atoms to the remainder of Formula ent-III, on one phenyl ring n is 2 and $(R^6)_n$ is 3-t-butyl-5-methyl, then $(R^6)_n$ on the other phenyl ring is other than 3-t-butyl-5-methyl; (c) when J is a $C_6$ cycloalkyl ring connected via adjacent carbon atoms to the remainder of Formula ent-III, on one phenyl ring n is 2 and $(R^6)_n$ is 3-t-butyl-5-t-butyl, then $(R^6)_n$ on the other phenyl ring is other than 3-t-butyl-5-t-butyl; and (d) when J is a 1,1'-binaphthalenyl ring system connected via the 2 and 2' positions to the remainder of Formula ent-III, then at least one n is an integer from 1 to 4.

This invention also involves a method of preparing a compound of Formula V,

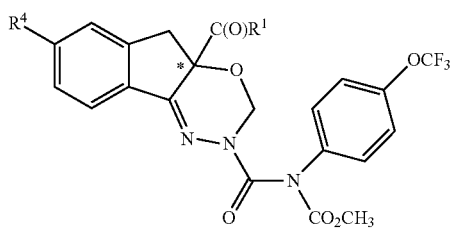

V wherein
$R^1$ is $C_1$-$C_3$ alkoxy; and
$R^4$ is F, $C_1$ or $C_1$-$C_3$ fluoroalkoxy;
using a compound of Formula Ia

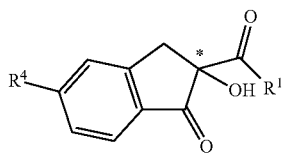

Ia wherein Formulae V and Ia are racemic or enantiomerically enriched at the chiral center indicated by *; characterized by:
preparing said compound of Formula Ia by the method indicated above.

DETAILED DESCRIPTION OF THE INVENTION

In the recitations herein, the term "alkyl", used either alone or in compound words such as "alkylthio" or "haloalkyl" includes straight chain or branched alkyl, such as, methyl, ethyl, n-propyl, i-propyl, or the different butyl, pentyl or hexyl isomers. "Alkenyl" includes straight chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkenyl" includes groups such as cyclopentenyl and cyclohexenyl as well as groups with more than one double bond such as 1,3- and 1,4-cyclohexadienyl. Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2OC(=O)$, $CH_3CH_2CH_2C(=O)$, $(CH_3)_2CHOC(=O)$ and the different butoxy or pentoxycarbonyl isomers. Other groups are defined analogously.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkoxy" and the like, are defined analogously to the term "haloalkyl". Examples of "haloalkenyl" include $(Cl)_2C=CHCH_2$ and $CF_3CH_2CH=CHCH_2$. Examples of "haloalkoxy" include $CF_3O$, $CCl_3CH_2O$, $HCF_2CH_2CH_2O$ and $CF_3CH_2O$.

The total number of carbon atoms in a substituent group can be indicated by the "$C_i$-$C_j$" prefix where, for example, i and j are numbers from 1 to 8. For example, $C_1$-$C_3$ alkyl designates methyl through propyl. When a compound is substituted with a substituent bearing a subscript that indicates the number of said substituents can exceed 1, said substituents (when they exceed 1) are independently selected from the group of defined substituents.

The term "member" in the description of a chain or ring refers to an atom forming part of the backbone structure of said chain or ring. If said chain or ring is said to be optionally substituted, the atom members are optionally substituted with one or more substituent groups, consistent with the atom members' free valency remaining after bonding of the atom members to form the chain or ring.

The term "optionally substituted" refers to a chain, ring or other group that is unsubstituted or substituted with at least one moiety other than hydrogen by replacement of said hydrogen.

The term "carbocyclic ring" denotes a ring wherein the atoms forming the ring backbone are selected only from carbon. The term "heterocyclic ring" denotes a ring wherein at least one atom forming the ring backbone is carbon and at least one other atom forming the ring backbone is other than carbon. The term "aryl" refers to an aromatic carbocyclic or heterocyclic ring to which is optionally fused one or more aromatic or nonaromatic rings. Aromatic indicates that each of ring atoms is essentially in the same plane and has a p-orbital perpendicular to the ring plane, and in which (4n+2)π electrons, when n is 0 or a positive integer, are associated with the ring to comply with Hückel's rule. A "ring system" refers to two or more fused rings. Examples of aromatic carbocyclic ring and ring systems include benzene, naphthalene, anthracene and the like. The term "heteroaromatic ring" means an aromatic heterocyclic ring. Examples of aromatic heterocyclic rings include thiophene, pyridine, pyridazine, pyrazine, pyrimidine, pyrrole, triazine, triazole and furan. A "nonaromatic heterocyclic ring" generally is a single ring with a backbone containing at least one carbon atom and one to four heteroatoms independently selected from the group nitrogen, oxygen and sulfur, provided that each ring contains no more than four nitrogens, no more than two oxygens and no more than two sulfurs. Said rings can be fully saturated heterocycles as well as partially or fully unsaturated heterocycles in which the Hückel rule for aromaticity is not satisfied by the ring. Examples of nonaromatic heterocyclic rings include tetrahydrofuran, thiolane, pyrrolidine, 1,3-dioxolane, 1,3-dithiolane, 1,3- and 1,4-dioxane, 4,5,6,7-tetrahydro-1,3-dioxepin and the like. Hetero-cyclic ring systems can be attached to other groups through any available carbon or nitrogen by replacement of a hydrogen on said carbon or nitrogen.

One skilled in the art will appreciate that not all nitrogen-containing heterocycles can form N-oxides, because the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

An asterisk (*) is used to indicate the Formula I hydroxylation center comprising the hydroxy group introduced by a process of this invention. When two of the groups attached to the hydroxylation center are identical a mirror plane of symmetry exists through the hydroxylation center. In this situation the hydroxylation center is achiral. If no mirror plane of symmetry exists through the hydroxylation center, then the hydroxylation center is a chiral center, resulting in two possible enantiomers corresponding to the two possible configurations at the chiral center. When the enantiomers are present in equal amounts the Formula I compound is racemic at the hydroxylation center; otherwise one enantiomer is present in excess and the Formula I compound is described as enantiomerically enriched at the hydroxylation center.

Furthermore, $R^1$, $R^2$ and $R^3$ of Formulae I and II can optionally comprise one or more additional chiral centers. $R^6$ of Formulae III and IV can also optionally comprise one or more chiral centers. A statement that Formula I is achiral, racemic or enantiomerically enriched at the hydroxylation center indicated by * refers only to that center. For example, a compound of Formula I that is racemic at the chiral center indicated by * can at the same time be enantiomerically enriched at other chiral centers.

For a general reference regarding enantiomers and enantioselective processes, see E. L. Eliel, S. H. Wilen and L. N. Mander, *Stereochemistry of Organic Compounds*, Wiley-Interscience, New York, 1994.

This invention pertains to a process for preparing compounds of Formula I by contacting a compound of Formula II with an oxidant and a zirconium complex, optionally in the presence of an inert solvent

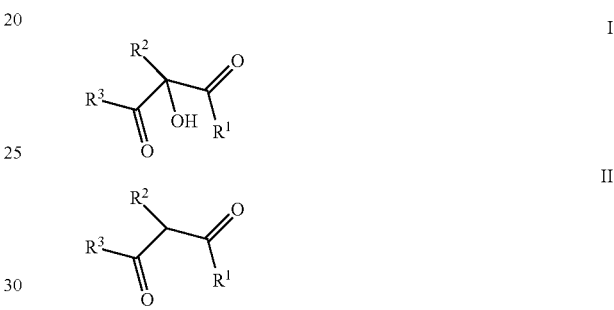

wherein * indicates the hydroxylation center, and $R^1$, $R^2$ and $R^3$ are as defined in the Summary of the Invention.

More specifically in this process, the compound of Formula I is prepared by contacting a compound of Formula II with generally about 0.9 to 10.0 equivalents or more of an oxidant in the presence of about 0.001 to 1.5 equivalents of a zirconium complex, and optionally an inert solvent. Typical reaction conditions include reaction temperatures in the range of about −5 to 100° C. and reaction times of about 2 hours to 8 days. Suitable oxidants include oxygen (e.g., air), hydrogen peroxide, monoethers of hydrogen peroxide including tert-butyl hydroperoxide, cumene hydroperoxide and combinations thereof, peracids such as peracetic acid or m-chloroperbenzoic acid, hypochlorites such as sodium hypochlorite, monopersulfates such as potassium monopersulfate (e.g., Oxone®), and dioxiranes such as dimethyldioxirane. A particularly useful oxidant for this process is hydrogen peroxide or a mono ether of hydrogen peroxide. A preferred oxidant is tert-butyl hydroperoxide. Suitable solvents include aliphatic hydrocarbons such as cyclohexane, aromatic hydrocarbons such as toluene, xylenes, ethylbenzene, mesitylene and cumene, halogenated hydrocarbons such as dichloromethane, dichloroethane and ortho-dichlorobenzene, ketones such as methyl ethyl ketone, methyl isobutyl ketone and methyl isopropyl ketone, esters such as methyl acetate, ethyl acetate, isopropyl acetate, alcohols such as methanol and 2-methyl-2-propanol, or ethers such as diethyl ether and tetrahydrofuran. Aromatic hydrocarbon solvents are preferred.

In one embodiment of this process, an achiral or racemic zirconium catalyst is used to prepare a compound of Formula I in racemic form. Suitable achiral or racemic zirconium complexes include zirconium alkoxide complexes such as zirconium(IV) isopropoxide, zirconium(IV) butoxide, zirconium(IV) tert-butoxide, and zirconium(IV) propoxide, zirconium(IV) β-dicarbonyl complexes such as zirconium(IV) acetylacetonate, zirconium(IV) aryloxide complexes, zirconium(IV) amine complexes, or zirconium(IV) amido complexes. Zirconium(IV) $C_1$-$C_4$ alkoxide and zirconium(IV) acetylacetonate are preferred, and zirconium(IV) isopropoxide and zirconium(IV) acetylacetonate are particularly useful. Zirconium(IV) acetylacetonate is most preferred because it is less hygroscopic than zirconium(IV) alkoxide complexes. For this racemic embodiment, hydrogen peroxide or a monoether of hydrogen peroxide is preferred as oxidant, and tert-butyl hydroxide is especially preferred as oxidant.

In another embodiment of the present invention, an enantiomerically enriched compound of Formula I is prepared by an enantioselective procedure. By "enantiomerically enriched" it is meant that a bulk sample of the compound contains an excess of either the (+) or (−) enantiomer and includes anything greater than a 1-to-1 (racemic) mixture of enantiomers up to and including 100% of the pure enantiomer. By definition, the enantiomeric excess (ee) of a sample is expressed as a percentage and is given by the equation Enantiomeric Excess=$[(En1-En2)\cdot 100\%]/(En1+En2)$ where En1 and En2 are the amounts of the two enantiomers. Thus, for example, an enriched compound having 25% (−) enantiomer and 75% (+) enantiomer is referred to as having a 50% enantiomeric excess of the (+) enantiomer. Enantiomerically enriched compounds of Formula I can be produced, for example, by physically separating the enantiomers of a racemic mixture according to standard methods. However, such methods are difficult to operate on a large scale and are often wasteful, because the undesired enantiomer must be discarded if it cannot be racemized. By "enantioselective" it is meant that the desired enantiomer of the chiral product is formed preferentially, although not necessarily exclusively. "Enantiomeric purity" is calculated the same way as enantiomeric excess; a product of 100% enantiomeric purity has one enantiomer in 100% excess and none of the other enantiomer; a product of 0% enantiomeric purity has equal amounts of enantiomers such that neither is in excess, and therefore the product is racemic.

For the embodiment of the present invention pertaining to a process for preparing enantiomerically enriched compounds of Formula I by contacting a compound of Formula II with an oxidant and a chiral zirconium complex, a reaction temperature of about 20 to 75° C. and tert-butyl hydroperoxide as oxidant are preferred. Chiral zirconium complexes suitable for this process including preferred chiral complexes comprising zirconium and ligands of Formula III or its enantiomer (ent-III) are described in further detail below.

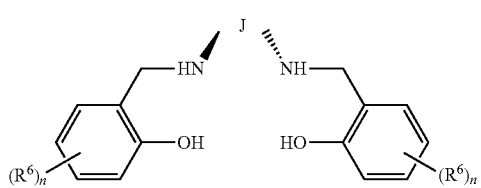

III

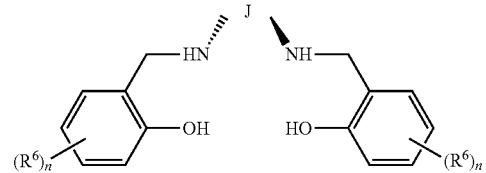

ent-III wherein J, $R^6$ and n are as defined in the Summary of the Invention.

$R^1$, $R^2$ and $R^3$ in Formulae I and II are appendages not directly involved in the hydroxylation reaction center. Because the reaction conditions of the hydroxylation process of the invention are so mild, a wide range of molecular structural features are possible for $R^1$, $R^2$ and $R^3$, and only functionalities most reactive to oxidative conditions are susceptible to being affected. Therefore the substituent radicals listed for $R^1$, $R^2$ and $R^3$ in the Summary of the Invention should be regarded as just describing a subgenus illustrative of the wide range of applicability of the process of this invention. Many of the radicals specified in the Summary of the Invention for $R^1$, $R^2$ and $R^3$ in Formulae I and II are optionally substituted. A wide range of optional substituents are possible; illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyl-oxy, cycloalkoxy, aryloxy, alkylthio, alkenylthio, alkynylthio, cycloalkylthio, arylthio, alkylsulfinyl, alkenylsulfonyl, alkynylsulfinyl, cycloalkylsulfinyl, arylsulfonyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenyl-aminocarbonyl, alkynylaminocarbonyl, arylaminocarbonyloxy, alkoxycarbonylamino, alkenyloxycarbonylamino, alkynyloxycarbonylamino and aryloxycarbonylamino, each further optionally substituted, and halogen, cyano and nitro. The optional further substituents are independently selected from groups like those illustrated above to give groups such as haloalkyl, haloalkenyl and haloalkoxy. As a further example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—$CH_2$—O—. Tying together a hydroxy group and the molecular structure to which it is attached can give cyclic ethers, including epoxides. Illustrative substituents also include oxygen, which when attached to carbon forms a carbonyl function. Preferred processes of the invention are those wherein in Formulae I and II, the carbon atom of $R^2$ connected to the center indicated by * is in the form of a methyl, methylene or carbonyl unit. When the connecting carbon of $R^2$ is in the form of a carbonyl unit, it forms a tricarbonyl system with the other two carbonyls of Formula II. The enhanced acidity of the tricarbonyl system can facilitate the hydroxylation of Formula II to give Formula I.

Although there is no definite limit to the sizes of Formulae I and II suitable for the processes of the invention, typically Formula II comprises 5-100, more commonly 5-50, and most commonly 5-25 carbon atoms, and 2-25, more commonly 2-15, and most commonly 2-10 heteroatoms. The heteroatoms are commonly selected from halogen, oxygen, sulfur, nitrogen and phosphorus, and more commonly, halogen, oxygen and nitrogen. Two heteroatoms in Formula II are the β-dicarbonyl oxygen atoms. The numbers of atoms commonly in Formula I are similar to those described by Formula II, except that as result of hydroxylation, Formula I has one more heteroatom. Also, there is no definite limit to the size of the illustrative groups listed for $R^1$, $R^2$ and $R^3$, but alkyl, including derivatives such as alkoxy, is commonly $C_1$-$C_6$, alkenyl and alkynyl are commonly $C_2$-$C_6$ and more commonly $C_2$-$C_6$, and cycloalkyl is commonly $C_3$-$C_8$.

One skilled in the art recognizes that sulfinyl and particularly thio moieties (m, for example, alkylthio, alkenylthio, alkynylthio, cycloalkylthio, arylthio, alkylsulfinyl, alkenylsulfinyl, alkynylsulfinyl, cycloalkylsulfinyl and arylsulfinyl substituents) are susceptible to oxidation. Thio- and sulfinyl-containing substituents in Formula II do not prevent the hydroxylation reaction of this invention, but thio can be converted to sulfinyl and sulfonyl, and sulfinyl converted to sulfonyl in the product of Formula I.

Of note are processes of this invention wherein, in Formulae I and II, $R^2$ is H, alkyl, cycloalkyl, a phenyl ring, or a 5- or 6-membered heteroaromatic ring, each ring optionally substituted; and $R^1$ and $R^3$ are not taken together. Of note also are processes of the invention wherein, in Formulae I and II, $R^1$ is H; or alkoxy, alkyl, cycloalkyl, a phenyl ring, a phenoxy ring or a 5- or 6-membered heteroaromatic ring, each optionally substituted; and $R^3$ is alkoxy, alkyl, cycloalkyl, a phenyl ring, or a 5- or 6-membered heteroaromatic ring, each optionally substituted.

Preferred processes of this invention are those wherein, in Formulae I and II, $R^1$ is alkyl or alkoxy, preferably alkoxy, more particularly $C_1$-$C_6$ alkoxy, and more preferably $C_1$-$C_3$ alkoxy, $R^2$ is preferably alkyl or alkylcarbonyl (alkyl substituted with oxygen on the linking carbon), more preferably alkyl and more particularly $C_1$-$C_6$ alkyl, $R^3$ is optionally substituted phenyl, or $R^2$ and $R^3$ are taken together to form an optionally substituted linking chain of 3 to 4 carbon members optionally fused to an optionally substituted phenyl ring. Preferably the optional substituents on phenyl are selected from halogen, cyano and nitro, and also alkyl, alkenyl, alkynyl, cycloalkyl, cycloalkenyl, aryl, formyl, alkylcarbonyl, alkenylcarbonyl, alkynylcarbonyl, alkoxycarbonyl, hydroxy, alkoxy, alkenyloxy, alkynyloxy, aryloxy, alkylsulfonyl, alkenylsulfonyl, alkynylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyloxy, alkenylaminocarbonyloxy, alkynylaminocarbonyloxy, arylaminocarbonyloxy, alkoxy-carbonylamino, the aforementioned substituents optionally tied together, the aforementioned substitutents optionally substituted with halogen. Particularly preferred processes of the invention are those wherein Formula I is Formula Ia and Formula II is Formula IIa

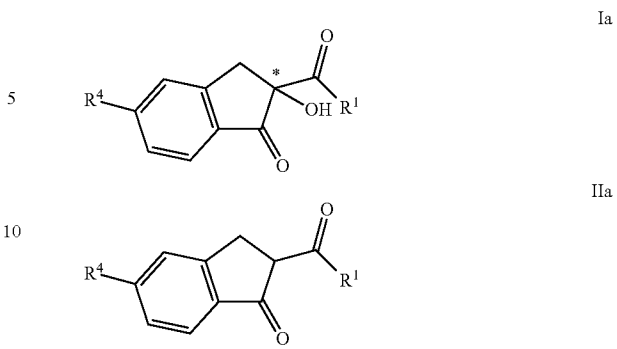

wherein * indicates the hydroxylation center, which is a chiral center, and Formula Ia is racemic or enantiomerically enriched.

Formulae Ia and IIa are subsets of Formula I and II, respectively, in which $R^2$ and $R^3$ are taken together to form a linking chain of 3 carbon members fused to a phenyl ring substituted with $R^4$. In Formulae Ia and IIa, $R^1$ is preferably alkoxy, more particularly $C_1$-$C_6$ alkoxy, and more preferably $C_1$-$C_3$ alkoxy; and $R^4$ is preferably halogen or haloalkoxy, more particularly F, Cl or $C_1$-$C_3$ fluoroalkoxy, and most particularly Cl.

Illustrating a combination of preferred $R^1$, $R^2$ and $R^3$ is a process for preparing a compound of Formula I that is racemic or enantiomerically enriched at the chiral center indicated by *, comprising contacting a compound of Formula II with a zirconium complex and an oxidant, wherein in Formulae I and II $R^1$ is alkoxy;
$R^2$ is alkyl;
$R^3$ is optionally substituted phenyl, or
$R^2$ and $R^3$ can be taken together to form an optionally substituted linking chain of 3 to 4 carbon members optionally fused to an optionally substituted phenyl ring.

Note that this preferred embodiment provides for the hydroxylation of β-keto esters.

A more preferred process of this invention is one wherein a compound of Formula IIa wherein $R^1$ is $C_1$-$C_3$ alkoxy and $R^4$ is F, Cl, or $C_1$-$C_3$ fluoroalkoxy is contacted with an oxidant and a zirconium complex to prepare a compound of Formula Ia that is racemic or enantiomerically enriched at the chiral center indicated by *.

Most preferred is a process in which a compound of Formula IIa is contacted with an oxidant and a chiral zirconium complex comprising zirconium and a ligand of Formula III or its enantiomer. Preparation of compounds of Formula Ia from compounds of Formula IIa has been previously reported in WO 95/29171 using a different process. The process of the instant invention provides higher yields of Formula Ia and is more convenient to run compared to the previously reported process. The process of the instant invention also affords improved enantioselectivity over the enantioselective process reported in WO 95/29171.

As already described, the hydroxylation process of this invention is generally applicable to a wide range of starting compounds of Formula II, which are obtainable through the methodologies known in the art of synthetic organic chemistry. For example, compounds of Formula IIa can be prepared by the methods described by R. Shapiro et al. "Toward the Manufacture of Indoxacarb" Chapter 17 (pp. 178-185 in *Synthesis and Chemistry of Agrochemicals VI* (ACS Symposium Series 800), American Chemical Society, Washington, D.C., 2002 and particularly PCT Publication WO 96/20151.

Another embodiment of this invention pertains to chiral zirconium complexes comprising zirconium and a chiral ligand of Formula III or its enantiomer (ent-III). The chiral centers of the chiral ligands of Formula III must provide overall chirality with the configurations of the NH linking groups as depicted, thereby excluding meso stereoisomers, which do not form enantiomers. The chiral zirconium complexes are suitable for the process for preparing enantiomerically enriched compounds of Formula I from Formula II. In the Summary of the Invention, rings (e.g., phenyl) and ring systems are described for J and $R^6$ in Formulae III and ent-III as being optionally substituted. As these optional substituents are spatially separate from the region of Formulae III and ent-III complexing to zirconium(IV), a wide range of substituents are possible, but at the same time, generally do not increase the usefulness of the zirconium complexes for the hydroxylation process of the invention. Optional substituents most easily included in Formulae III and ent-III are alkyl, haloalkyl, alkoxy, haloalkoxy, halogen and nitro; more particularly, $C_1$-$C_4$ alkyl, $C_1$-$C_4$ haloalkyl, $C_1$-$C_4$ alkoxy, $C_1$-$C_4$ haloalkoxy, halogen and nitro, and more preferably $C_1$-$C_4$ alkyl, $C_1$-$C_4$ alkoxy, halogen and nitro. Preferably, the optional substituents for the rings and ring systems described for J and $R^6$ are selected and positioned so that Formulae III and ent-III has a $C_2$ axis of symmetry. More preferably, the rings and ring systems in J and $R^6$ do not have optional substituents. Of note are compounds of Formulae III and ent-III wherein $R^6$ is other than the following: adamantyl, $C_3$-$C_6$ cycloalkyl optionally substituted with $C_1$-$C_2$ alkyl, $C_2$-$C_5$ alkylcarbonyloxy, $C_2$-$C_5$ alkoxycarbonyloxy, and optionally substituted phenylcarbonyloxy.

If the linking chain of J is fused to form a $C_3$-$C_8$ nonaromatic heterocyclic ring, preferably said nonaromatic heterocyclic ring is fully saturated; also preferably said ring is connected through carbon atoms of said ring to the aminomethyl moieties connecting to the remainder of Formulae III and ent-III. Illustrative examples of J include:

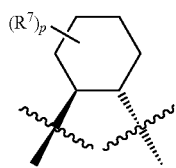
J-1

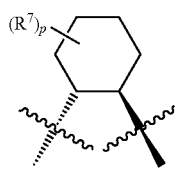
J-2

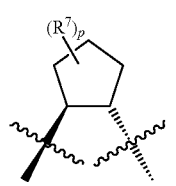
J-3

-continued

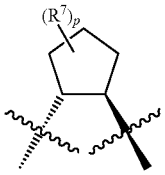
J-4

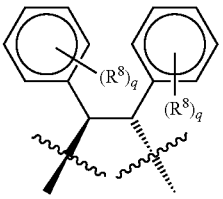
J-5

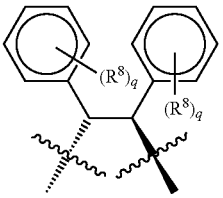
J-6

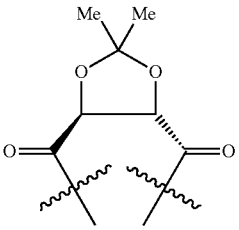
J-7

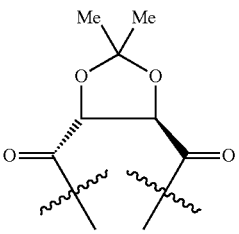
J-8

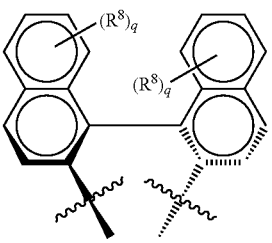
J-9

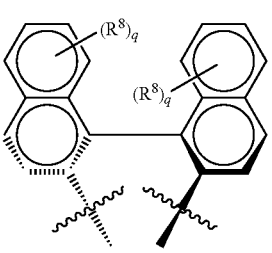
J-10

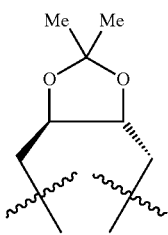

J-11

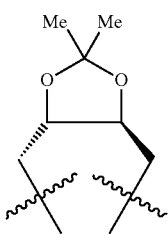

J-12

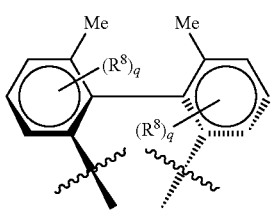

J-13

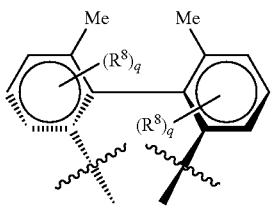

J-14 wherein
each $R^7$ is independently selected from $C_1$-$C_4$ alkyl, $C_1$-$C_4$ alkoxy and halogen;
each $R^8$ is independently selected from $C_1$-$C_4$ alkyl, $C_1$-$C_4$ alkoxy, halogen and nitro;
p is an integer from 0 to 4; and
each q is independently an integer from 0 to 3.
Preferably, each q is the same, and each $R^7$ and each $R^8$ are selected and positioned so that J has a $C_2$ axis of symmetry. More preferably, p and q are each 0.

The phrase "$C_6$ cycloalkyl ring connected via adjacent carbon atoms to the remainder of Formula III (or ent-III)" used herein refers to J-1 (or J-2) where p is 0. The phrase "1,1'-binaphthalenyl ring system connected via the 2 and 2' positions to the remainder of Formula III (or ent-III)" used herein refers to J-9 (or J-10) where q is 0.

Accordingly, for this embodiment of the invention, the chiral zirconium complex comprises a complex prepared from a chiral ligand of Formula III or its enantiomer and a zirconium complex. One skilled in the art will realize that the enantioselectivity of the hydroxylation reaction will generally decrease as the enantiomeric purity of the chiral ligand decreases. By the same reasoning, one skilled in the art will also realize that using a chiral ligand with greater than 0% enantiomeric purity (i.e. a chiral ligand that is enantiomerically enriched) may produce an enantiomerically enriched hydroxylation product. Preferably the enantiomeric purity of the chiral ligand is at least about 50%, more preferably at least 90%, even more preferably at least 95%, even more preferably at least 98%, and most preferably at least 99%.

The chiral zirconium complex can be prepared by contacting the zirconium complex with 0.1 to 5 equivalents of a compound of Formula III or ent-III, optionally in the presence of a solvent. Typical reaction conditions include reaction temperatures in the range of about −5 to 100° C. and reaction times of about 30 minutes to 3 days. Preferred chiral zirconium complexes comprise chiral ligands that have a $C_2$ axis of symmetry. As a substituent adjacent to the —OH function on each phenyl ring of Formula III (and ent-III) can promote stereoselectivity of the process, preferred are chiral zirconium complexes comprising ligands of Formula III or ent-III wherein each phenyl ring has an $R^6$ substituent ortho to the —OH function. More preferred are chiral zirconium complexes comprising ligands of Formula III or ent-III wherein each $R^6$ substituent ortho to the —OH function is tert-butyl. Particularly suitable ligands of Formula III or ent-III include structures where the HN-J-NH group is the diradical of (1S, 2S)- or (1R,2R)-1,2-cyclohexanediamine, (1S,2S)- or (1R, 2R)-1,2-diphenyl-1,2-ethanediamine (also known as (S,S)- or (R,R)-1,2-diphenylethylenediamine), (1S)- or (1R)-[1,1'-binaphthalene]-2,2'-diamine (also known as (S)- or (R)-1,1'-binaphthyl-2,2'-diamine), and (2S,3S)- or (2R,3R)-2,3-dihydroxybutanediamide (also known as (S,S)- or (R,R)-tartaric acid diamide). Preferred are chiral zirconium complexes comprising ligands comprising the diradical independently selected from the group consisting of (S,S)- or (R,R)-1,2-cyclohexanediamine and (S,S)- or (R,R)-1,2-diphenylethylenediamine.

Suitable zirconium complexes for the preparation of chiral zirconium complexes comprising zirconium and ligands of Formula III or ent-III include zirconium alkoxide complexes such as zirconium(IV) isopropoxide, zirconium(IV) butoxide, zirconium(IV) tert-butoxide, and zirconium(IV) propoxide, zirconium(IV) β-dicarbonyl complexes such as zirconium(IV) acetylacetonate, zirconium(IV) aryloxide complexes, zirconium(IV) amine complexes, or zirconium (IV) amido complexes. Zirconium(IV) isopropoxide and zirconium(IV) acetylacetonate are preferred. Suitable solvents for preparing the chiral zirconium complex include aliphatic hydrocarbons such as cyclohexane, aromatic hydrocarbons such as toluene, xylenes, ethylbenzene, mesitylene and cumene, halogenated hydrocarbons such as dichloromethane, dichloroethane and ortho-dichlorobenzene, ketones such as methyl ethyl ketone, methyl isobutyl ketone and methyl isopropyl ketone, esters such as methyl acetate, ethyl acetate, isopropyl acetate and ethers such as diethyl ether or tetrahydrofuran. Aromatic hydrocarbon solvents are preferred.

One skilled in the art will recognize that the process of this invention may involve several different chiral complexes comprising zirconium and a chiral ligand of Formula III or ent-III including those comprising additional ligands such as, but not limited to, the oxidant, compounds of Formula II and compounds of Formula I. All such complexes involved in the process of this invention are encompassed by this embodiment of the invention.

A particularly preferred complex is a complex comprising zirconium and a ligand of Formula IIIa

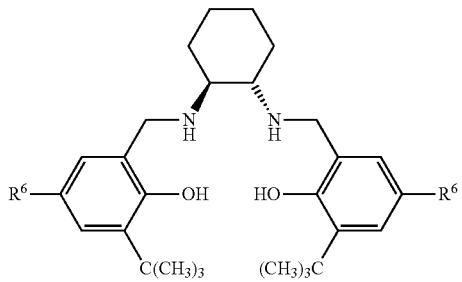

IIIa wherein each $R^6$ is the same and is selected from H and $C(CH_3)_3$.

The compound of Formula IIIa wherein $R^6$ is $C(CH_3)_3$ is named 2,2'-[(1S,2S)-1,2-cyclohexanediylbis(iminomethylene)]bis[4,6-bis(1,1-dimethylethyl)phenol], and the ligand of Formula IIIa wherein $R^6$ is H is named 2,2'-[(1S,2S)-1,2-cyclohexanediylbis(imino-methylene)]bis[6-(1,1-dimethylethyl)phenol].

A second particularly preferred complex is a complex comprising zirconium and a ligand of Formula IIIb IIIb wherein each $R^6$ is the same and is selected from H and $C(CH_3)_3$.

The ligand of Formula IIIb wherein $R^6$ is H is named 2,2'-[[(1S,2S)-1,2-diphenyl-1,2-ethanediyl]bis(iminomethylene)]bis[6-(1,1-dimethylethyl)phenol], and the ligand of Formula IIIb wherein $R^6$ is $C(CH_3)_3$ is named 2,2'-[[(1S,2S)-1,2-diphenyl-1,2-ethanediyl]-bis(iminomethylene)]bis[4,6-bis(1,1-dimethylethyl)phenol].

Other preferred complexes are complexes comprising zirconium and a ligand that is Formula ent-IIIa (which is the enantiomer of Formula IIIa)

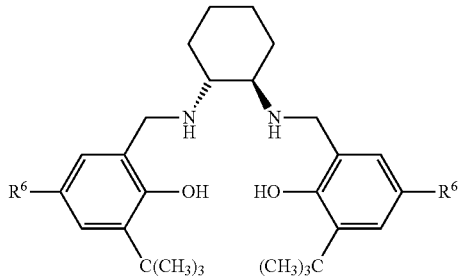

ent-IIIa wherein each $R^6$ is the same and is selected from H and $C(CH_3)_3$.

The ligand of Formula ent-IIIa wherein $R^6$ is $C(CH_3)_3$ is named 2,2'-[(1R,2R)-1,2-cyclo-hexanediylbis(iminomethylene)]bis[4,6-bis(1,1-dimethylethyl)phenol], and the ligand of Formula ent-IIIa wherein $R^6$ is H is named 2,2'-[(1R,2R)-1,2-cyclohexanediylbis(imino-methylene)]bis[6-(1,1-dimethylethyl)phenol].

Other preferred complexes are complexes comprising zirconium and a ligand that is Formula ent-IIIb (which is the enantiomer of Formula IIIb)

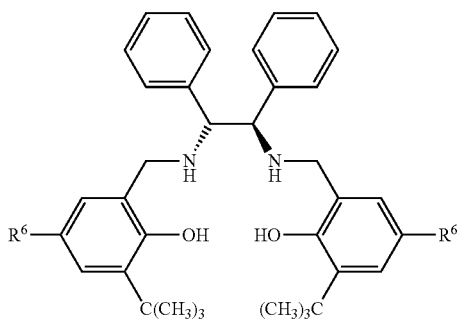

ent-IIIb wherein each $R^6$ is the same and is selected from H and $C(CH_3)_3$.

The ligand of Formula ent-IIIb wherein $R^6$ is H is named 2,2'-[[(1R,2R)-1,2-diphenyl-1,2-ethanediyl]bis(iminomethylene)]bis[6-(1,1-dimethylethyl)phenol], and the ligand of Formula IIIb wherein $R^6$ is $C(CH_3)_3$ is named 2,2'-[[(1R,2R)-1,2-diphenyl-1,2-ethanediyl]-bis(iminomethylene)]bis[4,6-bis(1,1-dimethylethyl)phenol].

Another embodiment of this invention pertains to the ligand of Formula III or its enantiomer ent-III. Preferred ligands of Formulae III or ent-III are those of the preferred chiral zirconium complexes. Particularly preferred are ligands of Formulae IIIa, ent-IIIa, IIIb and ent-IIIb. Most preferred are ligands of Formulae IIIa and IIIb, as the hydroxylation reaction of the invention involving a zirconium complex comprising a ligand selected from Formulae IIIa and IIIb is particularly useful for enantioselectively preparing the more efficacious S configuration of arthropodicidal oxadiazines of Formula V (depicted below).

Ligands of Formula III or ent-III can be prepared by general methods known in the art, such as those depicted in Scheme 1. Note that Formula III is illustrated in Scheme 1; preparation of ent-III can be accomplished by using the enantiomer of compounds of Formula 1 in the syntheses illustrated.

Scheme 1

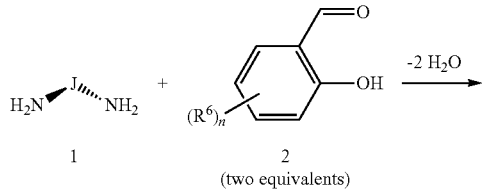

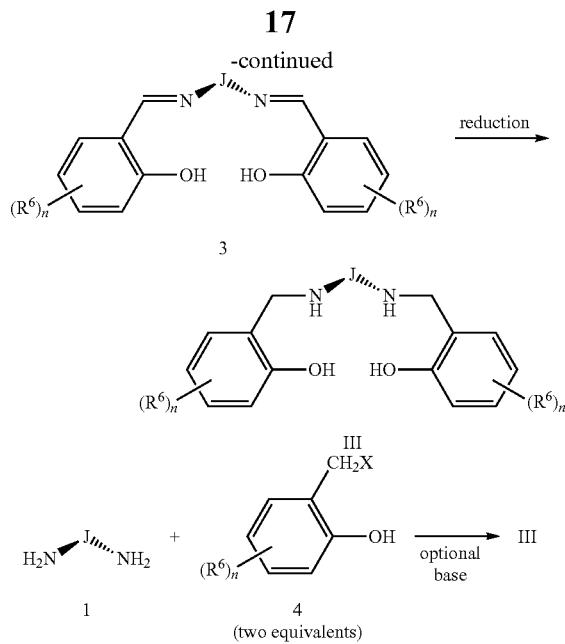

X is Cl, Br, I, OS(O)₂Z
Z is CH₃, CF₃ or p-C₆H₄CH₃

The first method involves the condensation of a chiral diamine of Formula 1, wherein J is defined as above for Formula III, with two equivalents of an appropriately substituted salicylaldehyde derivative of Formula 2 to form the Schiff base (imine) adduct of Formula 3 shown in Scheme 1. Excess amounts of compounds of Formula 2 may be used to facilitate this condensation. Subsequent reduction of the Schiff base with reagents such as sodium borohydride or sodium cyanoborohydride or by catalytic hydrogenation affords the desired ligands of Formula III. The reduction using sodium cyanoborohydride is conducted in the presence of acid, such as hydrochloric acid, in a suitable solvent, such as a mixture of ethanol and toluene.

Catalytic hydrogenation of compounds of Formula 3 to give the corresponding ligands of Formula III can be carried out using supported precious metal catalysts. Palladium- and platinum-based catalysts are preferred, with platinum being most preferred. Typical catalyst supports include carbon, alumina and calcium carbonate. Amorphous carbon supports, such as charcoal, are preferred. Any solvent compatible with the reaction conditions can be used, and preferably the solvent is aprotic. Particularly suitable solvents include aromatic hydrocarbon solvents such as toluene. The reaction can be promoted by the addition of a carboxylic acid (e.g., acetic acid) or mineral acid (e.g., sulfuric acid). Acetic acid is particularly useful because of its low corrosivity and ease of removal from the product solution. Best results are obtained when the reaction mixture is essentially free from water, which could otherwise cause hydrolysis of the Schiff base starting material. Therefore both the solvent and catalyst should be anhydrous.

Salicylaldehyde derivatives of Formula 2 are either commercially available or can be prepared by methods well known in the art. Another method for the preparation of a ligand of Formula III involves the reaction of a chiral diamine of Formula 1 with two equivalents of a benzyl halide or benzyl sulfonate of Formula 4. Optionally an additional base, such as organic bases such as triethylamine or inorganic bases such as sodium or potassium carbonate or sodium or potassium hydroxide may be used to facilitate this reaction. Excess amounts of compounds of Formula 4 may also be used to facilitate this reaction.

Ligands of Formula III can also be prepared from compounds of Formula IV by reduction of the C(=O)NH moiety using reducing agents such as lithium aluminum hydride (Scheme 2). Enantiomers of Formula III may be prepared by reduction of the enantiomers of Formula IV. Reductions of amides to amines are well known in the art; see, for example, J. March, *Advanced Organic Chemistry: Reactions, Mechanisms and Structure*, 3rd ed., 1985, Wiley, New York, p. 1099; and R. C. Larock, *Comprehensive Organic Transformations: A Guide to Functional Group Transformations*, 1989, VCH Publishers, Inc., pp. 432-434 and the references cited therein.

Scheme 2

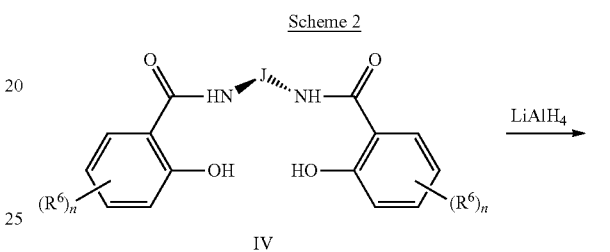

wherein J, n and $R^6$ are as defined for Formula III in the Summary of the Invention.

A synthesis of the ligand of Formula IIIa wherein $R^6$ is $C(CH_3)_3$ is described in Example 1, and syntheses of the ligand of Formula IIIb wherein $R^6$ is H is described in Examples 2 and 3.

As shown in Scheme 3, compounds of Formula IV can be prepared by condensing a chiral diamine of Formula 1 with suitable carboxylic acids or carboxylic acid derivatives such as acid chlorides and amides (Formula 5) or nitriles (Formula 6) using methods known to those skilled in the art, see for example, Richard C. Larock, *Comprehensive Organic Transformations: A Guide to Functional Group Transformations*, 1989, VCH Publishers, Inc., pp. 963-994 and the references cited therein.

Scheme 3

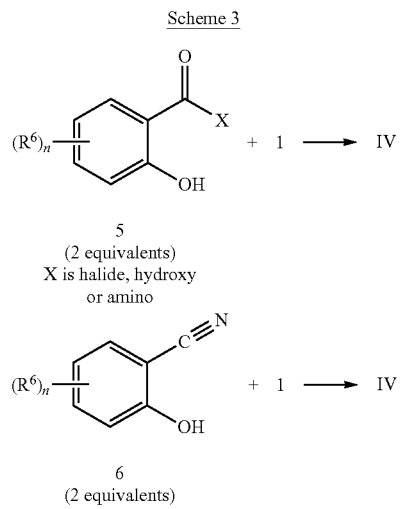

Preparation of a compound of Formula IV is illustrated in Example 4.

Carboxamide compounds of Formula IV can also be prepared by oxidizing the corresponding amine compounds of Formula III according to methods known in those skilled in the art; see for example, DE 871755, Ruhrchemie A. G., 1950; A. A. Frimer et al. *J. Org. Chem.* 1983, 48 (10), 1700; K. Tanaka et al. *Chem. Pharm. Bull.* 1987, 35 (1), 364; and G. Bettoni et al. *Tetrahedron* 1981, 37 (24), 4159.

Of note are complexes comprising zirconium and ligands of Formula IV and their enantiomers. Of particular note are compounds of Formula IVa and IVb and their enantiomers and complexes comprising them.

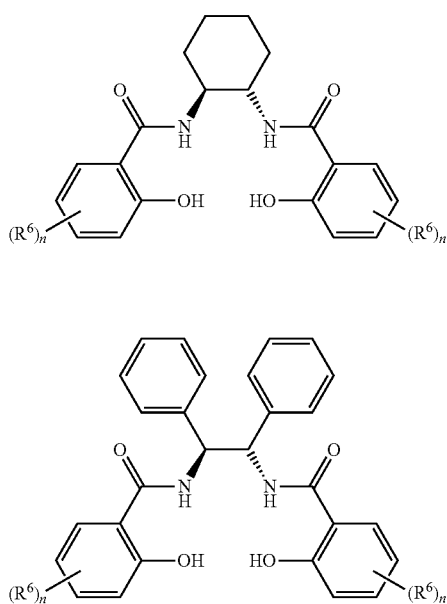

wherein n and $R^6$ are as defined for Formula III in the Summary of the Invention.

Of note are the use of compounds of Formula III or ent-III in other enantioselective processes including oxidations of sulfides to chiral sulfoxides, oxidations of olefins to chiral epoxides, dihydroxy compounds or aminoalkoxy compounds, and oxidations of allylic alcohols to epoxyalcohols. Complexes comprising compounds of Formula III or ent-III may also be used in enantioselective hydrogenations or reductions.

One skilled in the art will also recognize that compounds of Formula III and the intermediates described herein can be subjected to various electrophilic, nucleophilic, radical, organometallic, oxidation, and reduction reactions to add substituents or modify existing substituents.

It is recognized that some reagents and reaction conditions described above for preparing compounds of Formula III may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula III. One skilled in the art will also recognize that it may be necessary to perform a combination of the steps illustrated in the above schemes in an order other than that implied by the particular sequence presented to prepare the compounds of Formula III.

The hydroxylation method of the invention is useful for preparation of an arthropodicidal oxadiazine of Formula V, involving as process intermediate the compound of Formula Ia prepared by said hydroxylation method

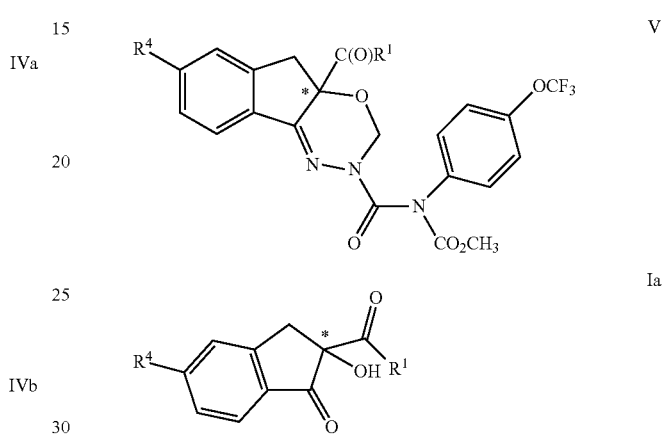

wherein Formulae V and Ia are racemic or enantiomerically enriched at the chiral center indicated by *, $R^1$ is $C_1$-$C_3$ alkoxy, and $R^4$ is F, Cl or $C_1$-$C_3$ fluoroalkoxy. Preferred because of excellent arthropodicidal efficacy of the oxadiazine product of Formula V is the aforementioned preparation wherein $R^1$ is $OCH_3$ and $R^4$ is Cl. As the enantiomer of Formula V having the S configuration has much greater arthropodicidal efficacy than does its antipode having the R configuration, preferred is the preparation wherein Formulae V and Ia are enantiomerically enriched with the S isomer obtained by hydroxylation using a chiral zirconium catalyst.

As already discussed, the compound of Formula Ia can be prepared from the corresponding compound of Formula IIa using the hydroxylation method of the invention. The further steps leading to the preparation of the compound of Formula V from Formula Ia are disclosed by R. Shapiro et al. "Toward the Manufacture of Indoxacarb" Chapter 17 (pp. 178-185 in *Synthesis and Chemistry of Agrochemicals VI* (ACS Symposium Series 800), American Chemical Society, Washington, D.C., 2002 and PCT Publications WO 92/11249, WO 95/29171, WO 96/31467 and WO 98/05656 and are depicted in Schemes 4 and 5. The reaction steps in these Schemes proceed substantially with retention of configuration at the chiral center indicated by *.

In the synthetic route shown in Scheme 4 the compound of Formula Ia is contacted with a protected hydrazine compound of Formula 7 to give the hydrazone of Formula 8. This hydrazone is then contacted with a formaldehyde equivalent (Formula 9) to form the cyclized compound of Formula 10. The protecting group is removed from the Formula 10 compound to give the compound of Formula 11, which is contacted with an acylating agent of Formula 12 to give the compound of Formula V.

Scheme 4

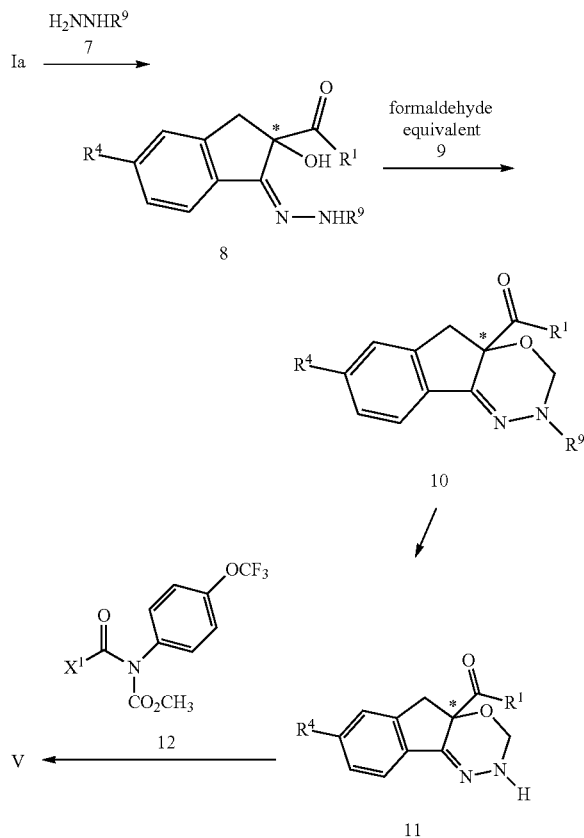

wherein $R^1$ and $R^4$ are as previously defined, $R^9$ is a protecting group, and $X^1$ is a leaving group.

The hydrazine derivative of Formula 7 has one end protected with protecting group $R^9$. A variety of amino protecting groups are known (see T. W. Greene and P. G. M. Wuts, *Protective Groups in Organic Synthesis,* 2nd ed.; Wiley: New York, 1991). A protecting group that is particularly convenient in this preparation is benzyloxycarbonyl ($R^9$ is C(O)OCH$_2$Ph). Generally at least a molar equivalent of the hydrazine of Formula 7 is used in relation to the ketone of Formula Ia. The condensation of the hydrazine of Formula 7 with the ketone of Formula Ia is greatly facilitated by the presence of a catalyst. Useful catalysts for this condensation have acidic properties. Such catalysts include zeolites such as molecular sieves, as well as Lewis acids and, most commonly, protic acids. Useful protic acids include, for example, mixed toluenesulfonic acids, p-toluenesulfonic acid, sulfuric acid or acetic acid. With strong protic acids such as the toluenesulfonic acids as little as about 10-12 mol % acid can provide high conversions. As strong acids can protonate the hydrazine derivative of Formula 7, generally the molar amount of Formula 7 should at least equal the sum of the molar amount of Formula Ia and the molar equivalents of acid catalyst. The condensation can be conducted without solvent or in the presence of an inert solvent such as methanol, isopropanol, tetrahydrofuran, dichloromethane, 1,2-dichloroethane, toluene and the like. Typical reaction conditions include temperatures of about 40 to 120° C., preferably about 65 to 85° C. for about 0.5 to 25 hours. The hydrazone of Formula 8 can be recovered by standard methods such as filtration, optionally after dilution of the reaction mixture with water. Alternatively, the reaction mixture containing the hydrazone of Formula 8 can be used directly in the next reaction step, or the hydrazone of Formula 8 can be extracted with solvent and the solvent extract used in the next reaction step.

In the next step the hydrazone of Formula 8 is cyclized using a formaldehyde equivalent (9) to give the compound of Formula 10. Formaldehyde equivalents include formaldehyde itself, but it readily polymerizes and is inconvenient to use. Other formaldehyde equivalents include halomethyl alkyl ethers. Most convenient of formaldehyde equivalents are dialkoxymethanes, preferably di($C_1$-$C_3$ alkoxy)methane, such as dimethoxymethane or diethoxymethane. The dialkoxymethane is preferably used in molar excess relative to Formula 8 and can also serve as the solvent. The reaction is optionally conducted using as co-solvent an inert solvent such as dichloromethane, trichloromethane, 1,2-dichloroethane, tetrahydrofuran, chlorobenzene, α,α,α-trifluorotoluene, toluene, heptane, xylenes, acetonitrile and the like. When the formaldehyde equivalent is a dialkoxymethane, the reaction is conducted in the presence of a Lewis or protic acid. Useful Lewis acids include phosphorus pentoxide, boron trifluoride or sulfur trioxide, of which 0.9 to 4.0 molar equivalents (relative to 8) is generally required for best results. Other useful Lewis acids include metal (especially scandium, ytterbium, yttrium and zinc) trifluoromethanesulfonates, which can be used in amounts of 0.1 to 0.5 molar equivalents relative to the compound of Formula 8. The most preferred Lewis acids for this step are phosphorus pentoxide and sulfur trioxide; the sulfur trioxide can be in the form of a complex such as SO$_3$.DMF (DMF is N,N-dimethylformamide), and usually there is also present a protic acid scavenger such as an amine complex (e.g., SO$_3$.pyridine). A filter aid such as Celite® (diatomaceous earth) can be advantageously added to reactions employing phosphorus pentoxide. When a Lewis acid is used, halogenated solvents are most suitable. Useful protic acids include mineral acids such as sulfuric and sulfonic acids such as aromatic, aliphatic and polymeric sulfonic acids; preferred protic acids include p-toluenesulfonic acid, mixtures of the isomeric sulfonic acids, benzenesulfonic acid, naphthalenesulfonic acids, xylenesulfonic acids, methanesulfonic acid, sulfuric acid, and camphorsulfonic acids; most preferred are p-toluenesulfonic acid and mixtures of isomeric toluenesulfonic acids. While stoichiometric or greater amounts of a protic acid can be employed, no more than a catalytic amount is needed. Preferably the amount of protic acid is about 0.01 to 0.20, more preferably between about 0.05 and 0.10, molar equivalents relative to the compound of Formula 8.

For the cyclization step, typical reaction conditions include temperatures of about 0 to 150° C., preferably about 40 to 70° C., more preferably about 50 to 60° C. with Lewis acids, and with protic acids such as toluenesulfonic acid preferably about 100 to 130° C., more preferably about 110 to 115° C., and pressures of about ambient pressure to 600 kPa above ambient pressure, preferably ambient pressure to 200 kPa above ambient pressure, and most conveniently near ambient pressure, for about 0.5 to 48 h. The byproduct alcohol is preferably removed by distillation during the reaction when a non-sacrificial Lewis acid such as a rare-earth trifluoromethanesulfonate or a protic acid is employed. The cyclized product of Formula 10 can be recovered by standard methods such as concentration, optionally preceded by quenching with aqueous base and extraction of the organic material, and crystallization from a suitable solvent such as ethanol for the reactions involving protic acids or liquid or gaseous Lewis acids such as sulfur trioxide or alternatively filtration, washing with aqueous base, concentration and crystallization for the phosphorus pentoxide reactions. The reaction mixture can also be filtered and used without further purification in the next reaction step. When metal trifluoromethanesulfonates are employed as the Lewis acid, the cyclized product can be recovered by concentrating the reaction mass, optionally diluting with an inert, water-immiscible solvent such as ethyl acetate, washing with water to remove the metal trifluoromethanesulfonates, concentrating the organic phase and inducing the product of Formula 10 to crystallize, optionally by adding a suitable solvent such as aqueous methanol, ethanol, hexane and the like.

In the next step, the protecting group $R^9$ is removed from the compound of Formula 10 to give the compound of Formula 11. Conditions for cleaving amino protecting groups are well known (see T. W. Greene and P. G. M. Wuts, *Protective Groups in Organic Synthesis,* 2nd ed.; Wiley: New York, 1991). The preferred benzyloxycarbonyl protecting group is most conveniently cleaved by hydrogenolysis. The reaction involves contacting a compound of Formula 11 wherein $R^9$ is $C(O)OCH_2Ph$ with hydrogen, from a hydrogen source or preferably molecular hydrogen itself, in the presence of a hydrogenolysis metal catalyst such as palladium, preferably supported on a substance such as charcoal, in an inert solvent such as methyl acetate, ethyl acetate, toluene or diethoxymethane. Typical reaction conditions include temperatures of about 0° C. to the boiling point of the solvent, preferably about 15 to 55° C., more preferably about 20 to 40° C., and pressures of close to ambient to about 350 kPa above ambient pressure, although higher pressures are also operable. The hydrogenolysis can be conveniently operated at near ambient pressure. Reaction time needed for complete conversion depends upon the usual parameters of temperature, hydrogen pressure, catalyst and reactant concentration, and typically requires 0.5 to 25 hours. The progress of the reaction can be monitored by analysis of the aliquots, or by consumption of hydrogen, as can be determined, for example, by pressure changes. The product of Formula 11 can be recovered from solution by standard methods such as filtering and collecting the metal catalyst for recycle to subsequent batches, separating the organic phase, concentrating by removing the solvent, and inducing crystallization of Formula 11, optionally by adding an aqueous $C_1$-$C_3$ alcohol, acetonitrile or an aliphatic hydrocarbon such as hexane. Preferably the compound of Formula 11 is used in the next step without isolation from the organic phase solution.

In the last step of Scheme 4, the compound of Formula 11 is contacted with about a molar equivalent of the acylating agent of Formula 12 to give the oxadiazine of Formula V. The group $X^1$ is selected from groups useful as leaving groups in nucleophilic displacement reactions. Considering ease of synthesis and cost, $X^1$ is preferably halide, and most preferably Cl. The reaction of the compound of Formula 11 with the acylating agent of Formula 12 is preferably conducted in the presence of about 1.0 to 1.5 molar equivalents (relative to Formula 11) of an acid scavenger such as a trialkylamine (e.g., triethylamine), N,N-dimethylaniline, pyridine or, preferably, aqueous sodium carbonate or bicarbonate, in an inert solvent such as toluene, xylene, methyl acetate, ethyl acetate, dichloromethane, trichloromethane, 1,2-dichloroethane, diethoxymethane and the like. The reaction is facile and can be conducted over a wide range of temperatures, e.g., about −10 to 60° C. Typical reaction conditions include temperatures of about 0 to 30° C. For convenience, the reaction can be conducted at ambient temperature (e.g., about 15 to 35° C.). The reaction is usually complete within several hours, and 1 to 2 h is typical. The product of Formula V can be recovered by standard methods such as washing the reaction mixture with aqueous acid or aqueous sodium chloride, concentrating the organic phase and inducing crystallization of V, optionally by addition of a $C_1$-$C_3$ alcohol, water, alcohol-water mixtures or an aliphatic hydrocarbon such as hexane.

The last two steps of Scheme 4 can be combined in a single reaction pot by adding the acylating agent of Formula 12 and the optional acid scavenger during the hydrogenolysis of the compound of Formula 10. In this way, the compound of Formula 11 is acylated as soon as it is formed to give the product of Formula V. Typical solvents for the combined steps are methyl acetate, ethyl acetate, toluene, xylene, dichloromethane, 1,2-dichloroethane and the like. Acid scavengers can be a tertiary amine, such as tripropylamine, tributylamine, diisopropylethylamine, N,N-dimethylaniline, N,N-diethylaniline, and the like, or a solid ionic compound such as sodium bicarbonate, calcium oxide, sodium pyrophosphate, citric acid trisodium salt and the like.

The sequence of condensation and acylation steps to convert the compound of Formula Ia to the compound of Formula V can also be conducted in other orders, as is illustrated by Scheme 5 below. In this alternate route, the compound of Formula Ia is contacted with hydrazine (13) to give the hydrazone of Formula 14. This hydrazone is then contacted with an acylating agent of Formula 12 to give the compound of Formula 15, which is then contacted with a formaldehyde equivalent (9) to give the compound of Formula V.

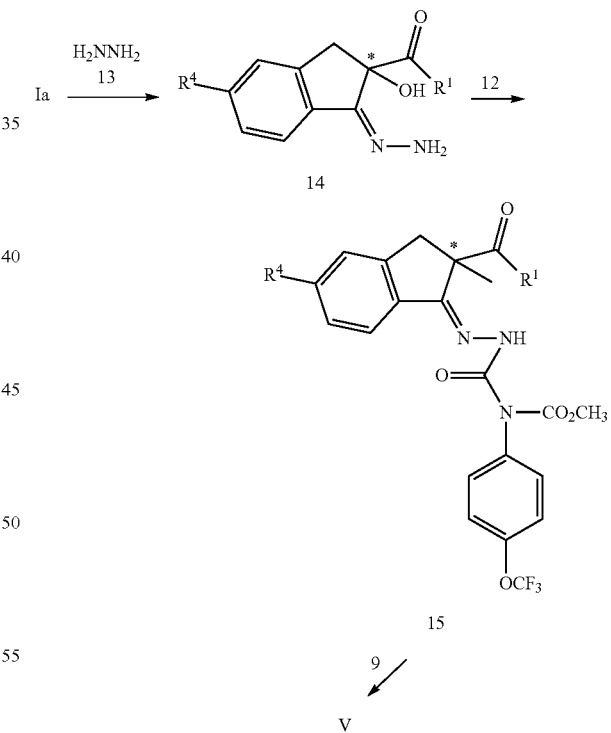

wherein the substituents are as defined for Scheme 4.

To prepare the hydrazone of Formula 14, the ketone of Formula Ia is contacted with preferably excess equivalents (e.g., 1.1 to 10 equivalents relative to Ia) of hydrazine, hydrazine monohydrate, hydrazine acetate, hydrazine hydrochloride and the like. The reaction is conducted in a solvent typically comprising methanol, ethanol, n-propanol, isopropanol and the like or acetic acid, and the reaction mixture is typically heated to the reflux temperature of the solvent. The reaction is generally complete within 24 hours. Step B of Example 2 of WO 92/11249 describes an example of this step.

The hydrazone of Formula 14 is then contacted with an acylating agent of Formula 12. This step is conducted using reaction conditions analogous to those already described for the conversion of the compound of Formula 11 to the compound of Formula V in Scheme 4. The product of Formula 15 is isolated by standard methods, such as aqueous work up, concentration and crystallization from a suitable solvent. Example 1 of WO 96/31467 provides an example of this step.

In the final step of Scheme 5, the compound of Formula 15 is treated with a formaldehyde equivalent of Formula 9. This step is conducted using reaction conditions analogous to those already described for the conversion of the compound of Formula 8 to the compound of Formula 10 in Scheme 4. Example 2 of WO 96/31467 provides an example of this step.

Acylating agents of Formula 12 can be prepared by contacting methyl [4-(trifluoromethoxy)phenyl]carbamate with a base such as sodium hydride, sodium methoxide and the like in a solvent comprising aromatic solvents such as benzene, toluene and the like and a ethereal solvent such as 1,2-dimethoxyethane to form the corresponding salt. The salt is then treated with the appropriate compound having formula X'C(O)X' to form Formula 12. For the preferred acylating agent of Formula 12 wherein $X^1$ is Cl, the appropriate compound is phosgene (ClC(O)Cl) or a phosgene substitute such as triphosgene (also named bis(trichloromethyl)carbonate). Most conveniently an excess of phosgene is used. Suitable temperatures for this reaction are in the range of about −10 to 100° C., preferably about −10 to 30° C. The reaction is usually complete within several hours. Acylating agents of Formula 12 wherein $X^1$ is other than Cl can be made from Formula 12 wherein $X^1$ is Cl by nucleophilic displacement. For example, treatment with silver fluoride can give Formula 12 wherein $X^1$ is F, and treatment with sodium iodide can give Formula 12 wherein $X^1$ is I. Methyl [4-(trifluoromethoxy)phenyl]carbamate can be made from 4-(trifluoromethoxy)benzenamine by standard methods, such as contacting 4-(trifluoromethoxy)benzenamine with methyl chloroformate in the presence of an acid scavenger such as N,N-diethylaniline, triethylamine, aqueous potassium carbonate and the like, optionally in a solvent such as diethyl ether, dichloromethane and the like. Suitable temperatures for this reaction are typically in the range of about 0 to 100° C., with temperatures of about 20 to 70° C. being preferred. The reaction is usually complete within several hours. Example 1 of WO 96/31467 provides an example of preparation of the preferred acylating agent of Formula 12 wherein $X^1$ is Cl.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet, and "br m" means broad multiplet. Chemoselectivity is the percentage of the consumed limiting reagent (i.e. IIa in Examples 5-11) that is converted into product.

In the Examples, quantitative HPLC analysis was used to measure the amounts of methyl 5-chloro-2,3-dihydro-2-hydroxy-1-oxo-1H-indene-2-carboxylate and methyl 5-chloro-2,3-dihydro-1-oxo-1H-indene-2-carboxylate present in the reaction mixture. In the examples where a chiral zirconium complex was used, a chiral HPLC method was used to determine the enantiomeric excess of methyl 5-chloro-2,3-dihydro-2-hydroxy-1-oxo-1H-indene-2-carboxylate.

The quantitative HPLC analyses were conducted using a Supelco (595 North Harrison Road, Bellefonte, Pa. 16823-0048 USA) Discovery C8 (octylsilane bonded to silica) column (25 cm×4.6 mm, 5 µm) and a flow rate of 1.5 mL/min at 40° C. The elution solvent was a mixture of water (pH 6.5) and acetonitrile, with the concentration of acetonitrile increased from 32% to 75% over 30 minutes to produce a solvent gradient. Detection utilized light absorption at 260 nm. The detector was calibrated using an external standard with 3-point calibration curves for methyl 5-chloro-1,3-dihydro-2-hydroxy-1-oxo-2H-indene-2-carboxylate and methyl 5-chloro-1-oxo-2,3-dihydroindene-2-carboxylate.

The chiral HPLC analyses were conducted using an Astec (Advanced Separation Technologies, Inc., 37 Leslie Court, Whippany, N.J. 07981 USA) Chirobiotic T™ (teicoplanin glycopeptide covalently bound to 5 µm silica gel) column and a flow rate of 1.0 mL/min at 40° C. The elution solvent was an isocratic 80:20 mixture of hexanes and ethanol. Detection utilized light absorption at 254 and 230 nm. Calibration was not necessary as the peak areas of the two enantiomers are directly compared and the detector sensitivity does not differ between enantiomers.

EXAMPLE 1

Preparation of the 2,2'-[(1S,2S)-1,2-cyclohexanediyl-bis(iminomethylene)]bis[4,6-bis(1,1-dimethylethyl) phenol] (Formula IIIa wherein $R^6$ is $C(CH_3)_3$)

An ethanolic hydrochloric acid solution was prepared by dissolving commercial concentrated hydrochloric acid (1.596 g, 37% by weight, 16.2 mmol) in ethanol (15 mL). Solid sodium cyanoborohydride (1.850 g, 29.4 mmol) and the ethanolic hydrochloric acid were added in portions over 1.5 hours to a slurry of 2,2'-[(1S,2S)-1,2-cyclohexanediyl-bis(nitrilomethylidyne)]bis[4,6-bis(1,1-dimethylethyl)phenol] (also known as (1S,2S)-(+)-1,2-cyclohexanediamino-N,N'-bis(3,5-di-t-butylsalicylidene) (Strem, 4.026 g, 7.362 mmol) in ethanol (50 mL) and toluene (15 mL) at 65° C. The reaction mixture changed from a cloudy, yellow suspension to a cloudy white solution during this time. The reaction mixture was stirred for an additional 30 minutes at 65° C. and then poured into a mixture of ethyl acetate and aqueous sodium bicarbonate solution. The aqueous layer was separated and extracted with more ethyl acetate. The combined organic extracts were dried (MgSO$_4$), filtered, and evaporated in vacuo. The remaining crude product was purified by flash chromatography over silica gel (90:10 hexanes-ethyl acetate). After drying in vacuo, the purified product was obtained as a white solid (3.262 g, 80% yield) melting 128-132° C. $^1$H NMR (CDCl$_3$) δ 1.279 (s, 18H, overlapped with broad resonances 1.20-1.30 ppm, approx. 6H integration), 1.42 (m, 2H), 1.375 (s, 18H), 1.70 (br m, 2H), 2.46 (br m, 2H), 2.17 (br m, 2H), 3.898 (d of AB pattern, J=13.3 Hz, 2H), 4.039 (d of AB pattern), J=13.3 Hz, 2H), 6.863 (d, J=2.3 Hz, 2H), 7.208 (d, J=2.5 Hz, 2H). LC/MS AP$^+$: 8.33 min, 551 (M$^+$+1); AP$^-$: 8.35 min, 549 (M$^+$−1).

EXAMPLE 2

Preparation of 2,2'-[[(1S,2S)-1,2-diphenyl-1,2-ethanediyl]bis(iminomethylene)]bis[6-(1,1-dimethylethyl)phenol] (IIIb wherein $R^6$ is H) using sodium cyanoborohydride (1S,2S)-1,2-diphenyl-1,2-ethanediamine (also known as (1S,2S)-(−)-1,2-diphenyl-ethylenediamine) (2.04 g, 9.40 mmol) and 3-(1,1-dimethylethyl)-2-hydroxybenzaldehyde (also known as 3-tert-butyl-2-hydroxy-benzaldehyde) (3.36 g, 18.8 mmol, 2 equivalents) were heated at reflux in methanol (50 ml) for 1 hour. The mixture was then cooled to 65° C., and sodium cyanoborohydride (1.50 g, 23.9 mmol, 2.5 mole per mole of the starting diamine) and concentrated hydrochloric acid (36.5%, 2.07 g, 20.7 mmol, 2.2 mole per mole of the starting diamine) dissolved in ethanol (10 mL) were added portionwise over 10-15 minutes. After the addition, the mixture was held at 65° C. for 30 minutes. The mixture was then cooled, poured onto a mixture of saturated aqueous sodium bicarbonate solution (40 mL) and ethyl acetate (50 mL). About 40 mL of water was added to dissolve the salt. The organic layer was separated, and the aqueous layer was extracted with ethyl acetate (3×50 mL). The combined organic layer was dried (MgSO$_4$), and the solvent evaporated to give a glassy residue, which was triturated with absolute ethanol to give the title compound as the first crop (2.98 g). Concentration of the filtrate gave a second crop (0.45 g), for a total of the title product of 3.43 g (68.6% yield) melting at 143-145° C. $^1$H NMR (CDCl$_3$) δ 1.35 (s, 18H), 2.2 (br m, 2H), 3.52 (d, J=13.5 Hz, 2H), 3.76 (d, J=13.5 Hz, 2H), 3.92 (s, 2H), 6.5 (m, 4H), 6.8 (m, 4H), 7.0-7.2 (m, 8H), 10.4 (br s, 2H).

EXAMPLE 3

Preparation of 2,2'-[[(1S,2S)-1,2-diphenyl-1,2-ethanediyl]bis(iminomethylene)]bis[6-(1,1-dimethylethyl)phenol] (IIIb wherein $R^6$ is H) using hydrogenation Step A Preparation of 2,2'-[[(1S,2S)-1,2-diphenyl-1,2-ethanediyl]bis(nitrilo-methylidyne)]bis[6-(1,1-dimethylethyl)phenol]

(1S,2S)-1,2-diphenyl-1,2-ethanediamine (also known as (1S,2S)-(−)-1,2-diphenyl-ethylenediamine) (20.8 g, 98 mmol) and 3-(1,1-dimethylethyl)-2-hydroxybenzaldehyde (also known as 3-tert-butyl-2-hydroxy-benzaldehyde) (35.0 g, 196 mmol, 2 equivalents) were heated in methanol (150 mL). As the mixture approached reflux temperature, a gum separated out. Methanol (50 g) and heptane (10 g) were added and the gummy solids broken up with a spatula. The mixture was heated at reflux for two hours and then allowed to cool to room temperature. The product was collected by filtration and washed with methanol to give the title product as a bright yellow solid. Concentration of the filtrate provided a second crop (8.20 g).

Step B Preparation of 2,2'-[[(1S,2S)-1,2-diphenyl-1,2-ethanediyl]bis(imino-methylene)]bis[6-(1,1-dimethylethyl)phenol]

A 100-mL stainless steel autoclave was charged with 2,2'-[[(1S,2S)-1,2-diphenyl-1,2-ethanediyl]bis(nitrilomethylidyne)]bis[6-(1,1-dimethylethyl)phenol] (i.e. the product of Step A, 5.0 g), platinum-on-carbon catalyst (Engelhard Corporation CP97 Lot #6729-36-02, 3 weight %, 2.5 g), toluene (45.0 g), and glacial acetic acid (1.0 g). After flushing with nitrogen, the vessel was pressurized to 100 psig (690 kPa) above ambient with hydrogen and heated to 75° C. After reaching 75° C., the hydrogen pressure was adjusted to about 400 psig (2760 kPa) and the reaction mixture held at 75° C. and about 400 psig (2760 kPa) for 5 h. The mixture was cooled to 20° C., and the hydrogen was vented, resulting in some loss of product. The catalyst was removed by filtration, and the reactor and catalyst were washed with toluene (300 grams). The product solution was washed successively with saturated aqueous sodium bicarbonate (2×100 mL) and water (150 mL) and dried over anhydrous magnesium sulfate. The organic phase was concentrated under reduced pressure to leave a dark oil (5.0 g). Addition of methanol (12 g) dissolved the oil and induced crystallization. The crystals were collected, washed with methanol (5 g) and dried in a vacuum oven at 45° C. to give the title product (3.0 g) melting at 143-144° C.

EXAMPLE 4

Preparation of N,N-(1S,2S)-1,2-cyclohexanediylbis[3,5-bis(1,1-dimethylethyl)-2-hydroxy-benzenecarboxamide (IVa wherein $(R^6)_n$ is 3,5-di-tert-butyl)

Thionyl chloride (5.95 g, 50 mmol) was added to a mixture of 3,5-bis(1,1-dimethylethyl)-2-hydroxybenzoic acid (alternatively named 3,5-di-tert-butylsalicylic acid) (2.50 g, 10 mmol) and N,N-dimethylformamide (10 drops) in dry toluene (50 mL) at 60° C. After 1 hour at 60° C., the light yellow solution was evaporated in vacuo to leave a thick oil and then diluted with dry tetrahydrofuran (THF) (40 mL). After heating to 50° C., a solution of (1S,2S)-(+)-1,2-cyclohexanediamine (0.560, 4.90 mmol) in 10 mL of dry THF was added followed by triethylamine (1.01 g, 10 mmol). After 1 h at 50° C., the reaction mixture was quenched with water (25 mL) and then poured into ethyl acetate/water. The organic phase was separated, and the aqueous phase extracted with additional ethyl acetate (35 mL). The combined organic phase was washed once more with water and then evaporated onto silica gel. Purification by flash chromatography (hexanes-ethyl acetate, 0 to 20% ethyl acetate over 1 hour) and evaporation of the chromatography solvent in vacuo afforded the product as a foamy off-white solid (1.18 g). The product was further purified by stirring the white solid in methanol (5 mL) and then decanting the mother liquor from a small amount of insoluble, gummy solids. Evaporation of the methanol mother liquor afforded the title product as an off-white solid (1.15 g). $^1$H NMR (CDCl$_3$) δ 1.29 (s, 18H), 1.38 (s, 18H), 1.82 (s, 2H), 2.22 (br s, 2H), 3.96 (br s, 2H), 6.95 (br s, 2H), 7.16 (d, J=2 Hz, 2H), 7.41 (d, J=2 Hz, 2H), 12.70 (s, 2H). MS ESI Positive: 579 (M+1), ESI Negative: 577 (M−1).

EXAMPLE 5

Preparation of racemic methyl 5-chloro-2,3-dihydro-2-hydroxy-1-oxo-1H-indene-2-carboxylate (Formula Ia wherein $R^1$ is OCH$_3$ and $R^4$ is Cl)

To a solution of methyl 5-chloro-2,3-dihydro-1-oxo-1H-indene-2-carboxylate (also known as methyl 5-chloro-1-oxo-2,3-dihydroindene-2-carboxylate) (0.500 g, 2.23 mmol) (Formula IIa wherein $R^1$ is OCH$_3$ and $R^4$ is Cl) and zirconium (IV) isopropoxide (0.0086 g, 0.022 mmol) in toluene (1.34 g, 1.56 mL) at 30° C. was added an aqueous solution of tert-butyl hydroperoxide (70%, 0.316 g, 2.46 mmol). The reaction mixture was stirred for 24 hours at 30° C. and then diluted with acetonitrile (about 6 mL). Quantitative HPLC analysis showed 92% conversion of methyl 5-chloro-2,3-dihydro-1-oxo-1H-indene-2-carboxylate, forming racemic methyl 5-chloro-2,3-dihydro-2-hydroxy-1-oxo-1H-indene-2-carboxylate in 89% yield (97% chemoselectivity).

EXAMPLE 6

Preparation of racemic methyl 5-chloro-2,3-dihydro-2-hydroxy-1-oxo-1H-indene-2-carboxylate (Formula Ia wherein $R^1$ is $OCH_3$ and $R^4$ is Cl)

The reaction described in Example 1 was carried out using zirconium(IV) acetylacetonate (0.0544 g, 0.112 mmol). Quantitative HPLC analysis showed 97% conversion of methyl 5-chloro-2,3-dihydro-1-oxo-1H-indene-2-carboxylate, forming racemic methyl 5-chloro-2,3-dihydro-2-hydroxy-1-oxo-1H-indene-2-carboxylate in 93% yield (96% chemoselectivity).

EXAMPLE 7

Preparation of racemic methyl 5-chloro-2,3-dihydro-2-hydroxy-1-oxo-1H-indene-2-carboxylate (Formula Ia wherein $R^1$ is $OCH_3$ and $R^4$ is Cl)

The reaction described in Example 5 was carried out using zirconium(IV) tert-butoxide (0.0428 g, 0.112 mmol). Quantitative HPLC analysis showed 94% conversion of methyl 5-chloro-2,3-dihydro-1-oxo-1H-indene-2-carboxylate, forming racemic methyl 5-chloro-2,3-dihydro-2-hydroxy-1-oxo-1H-indene-2-carboxylate in 82% yield (87% chemo-selectivity).

EXAMPLE 8

Preparation of methyl (2S)-5-chloro-2,3-dihydro-2-hydroxy-1-oxo-1H-indene-2-carboxylate (also known as (+)-methyl 5-chloro-2,3-dihydro-2-hydroxy-1-oxo-1H-indene-2-carboxylate) (Formula Ia wherein $R^1$ is $OCH_3$ and $R^4$ is Cl)

A chiral zirconium complex was prepared by stirring zirconium(IV) isopropoxide (0.0345 g, 0.089 mmol) with 2,2'-[(1S,2S)-1,2-cyclohexanediylbis(iminomethylene)]bis[4,6-bis(1,1-dimethylethyl)phenol] (Formula IIIa wherein $R^6$ is $C(CH_3)_3$, 0.0613 g, 0.11 mmol) in toluene (2 mL) at ambient temperature. After stirring overnight, the homogeneous solution was evaporated to dryness in vacuo, and the residue redissolved in toluene (1.34 g). Methyl 5-chloro-2,3-dihydro-1-oxo-1H-indene-2-carboxylate (0.250 g, 1.11 mmol) (Formula IIa wherein $R^1$ is $OCH_3$ and $R^4$ is Cl) was added to the toluene solution, the solution was heated to 55° C., and then an aqueous solution of tert-butyl hydroperoxide (70%, 0.316 g, 2.46 mmol) was added. After 2 hours at 55° C., the solution was diluted with acetonitrile (11.5 mL). Analysis by quantitative and chiral HPLC showed 100% conversion of methyl 5-chloro-2,3-dihydro-1-oxo-1H-indene-2-carboxylate, forming methyl 5-chloro-2,3-dihydro-2-hydroxy-1-oxo-1H-indene-2-carboxylate in 84% yield (84% chemoselectivity) and 84% enantiomeric excess of the S-enantiomer.

EXAMPLE 9

Preparation of methyl (2S)-5-chloro-2,3-dihydro-2-hydroxy-1-oxo-1H-indene-2-carboxylate (Formula Ia Wherein $R^1$ is $OCH_3$ and $R^4$ is Cl)

The reaction described in Example 8 was carried out using methyl 5-chloro-2,3-dihydro-1-oxo-1H-indene-2-carboxylate (0.100 g, 0.445 mmol) (Formula IIa wherein $R^1$ is $OCH_3$ and $R^4$ is Cl). Analysis by quantitative and chiral HPLC showed 100% conversion of methyl 5-chloro-2,3-dihydro-1-oxo-1H-indene-2-carboxylate, forming methyl 5-chloro-2,3-dihydro-2-hydroxy-1-oxo-1H-indene-2-carboxylate in 66% yield (66% chemo-selectivity) and 90% enantiomeric excess of the S-enantiomer.

EXAMPLE 10

Preparation of methyl (2S)-5-chloro-2,3-dihydro-2-hydroxy-1-oxo-1H-indene-2-carboxylate (Formula Ia Wherein $R^1$ is $OCH_3$ and $R^4$ is Cl)

A chiral zirconium complex was prepared by stirring zirconium(IV) isopropoxide (0.560 g, 1.44 mmol) with 2,2'-[(1S,2S)-1,2-cyclohexanediylbis(iminomethylene)]bis[4,6-bis(1,1-dimethylethyl)phenol] (Formula IIIa wherein $R^6$ is $C(CH_3)_3$, 1.00 g, 1.82 mmol) for 30 minutes in toluene (25 mL) at ambient temperature. The homogeneous solution was evaporated to dryness in vacuo, and the residue redissolved in toluene (8.70 g, 10 mL). A toluene solution of methyl 5-chloro-2,3-dihydro-1-oxo-1H-indene-2-carboxylate (1.53 g of a 21.55% by weight toluene solution, 1.47 mmol of methyl 5-chloro-2,3-dihydro-1-oxo-1H-indene-2-carboxylate) was added to the toluene solution of the chiral zirconium complex and the reaction mixture was heated to 55° C. Over the next 47 minutes, a toluene solution of methyl 5-chloro-2,3-dihydro-1-oxo-1H-indene-2-carboxylate (36.71 g of a 21.55% by weight toluene solution, 35.2 mmol of methyl 5-chloro-2,3-dihydro-1-oxo-1H-indene-2-carboxylate) and, simultaneously, an aqueous solution of tert-butyl hydroperoxide (70%, 4.69 g, 36.4 mmol) were co-fed to the reaction mixture at 55° C. After the two solutions were added, the reaction mixture was heated at 55° C. for an additional 6 hours, cooled to 25° C., and then filtered. After drying, 4.64 g (52.5%) of the S-enantiomer of methyl 5-chloro-2,3-dihydro-2-hydroxy-1-oxo-1H-indene-2-carboxylate was obtained as a white solid in 98% enantiomeric excess. Quantitative HPLC analysis of the filtrate and solids showed that the overall reaction proceeded with 85% conversion of methyl 5-chloro-2,3-dihydro-1-oxo-1H-indene-2-carboxylate, forming methyl 5-chloro-2,3-dihydro-2-hydroxy-1-oxo-1H-indene-2-carboxylate in 74% yield (87% chemoselectivity) and 75% enantiomeric excess of the S-enantiomer.

EXAMPLE 11

Preparation of methyl (2S)-5-chloro-2,3-dihydro-2-hydroxy-1-oxo-1H-indene-2-carboxylate (Formula Ia Wherein $R^1$ is $OCH_3$ and $R^4$ is Cl)

A chiral zirconium complex was prepared by rapidly stirring (forming a vortex) a mixture of zirconium(IV) acetylacetonate (43.5 mg, 0.089 mmol) and 2,2'-[[(1S,2S)-1,2-diphenyl-1,2-ethanediyl]bis(iminomethylene)]bis[6-(1,1-dimethylethyl)-phenol] (Formula Mb wherein $R^6$ is H, 0.096 g, 0.18 mmol) in toluene (1.00 mL) at 50° C. for one hour. The resulting solution was evaporated to dryness in vacuo, then a solution of methyl 5-chloro-2,3-dihydro-1-oxo-1H-indene-2-carboxylate (0.500 g, 2.23 mmol) (Formula IIa wherein $R^1$ is $OCH_3$ and $R^4$ is Cl) in toluene (2.00 mL) was added. The reaction mixture was heated to 65° C., and then an aqueous solution of tert-butyl hydroperoxide (70%, 0.316 g, 0.340 mL, 2.46 mmol) was added. After 3.5 hours at 65° C., the reaction was quenched by adding an acetonitrile solution (7.00 mL) containing biphenyl (0.125 g) as an HPLC internal standard and cooling to ambient temperature. Analysis by quantitative and chiral HPLC showed 100% conversion of methyl 5-chloro-2,3-dihydro-1-oxo-1H-indene-2-carboxylate, forming methyl 5-chloro-2,3-dihydro-2-hydroxy-1-oxo-1H-indene-2-carboxylate in 85% yield (85% chemoselectivity) and 94% enantiomeric excess of the S-enantiomer.

EXAMPLE 12

Preparation of methyl (2S)-5-chloro-2,3-dihydro-2-hydroxy-1-oxo-1H-indene-2-carboxylate (Formula Ia wherein $R^1$ is $OCH_3$ and $R^4$ is Cl) with recycle of catalyst A chiral zirconium complex was prepared by stirring zirconium(IV) acetylacetonate (0.73 g, 1.5 mmol) with IIIb wherein $R^6$ is H (1.61 g, 3.0 mmol) in toluene (5 mL) for 1 hour at 50° C. To the resulting solution was added methyl 5-chloro-2,3-dihydro-1-oxo-1H-indene-2-carboxylate (4.5 g, 20 mmol) and additional toluene (4 mL). The temperature was increased to 65° C., and then two separate solutions of methyl 5-chloro-2,3-dihydro-1-oxo-1H-indene-2-carboxylate (17.96 g, 80 mmol in 53 g of toluene) and a 70% by weight solution of tert-butyl hydroperoxide in water (11.59 g, 90 mmol) were simultaneously co-fed to the reaction mixture. The rates of addition were controlled so that the tert-butyl hydroperoxide feed was completed in 30 minutes and the methyl 5-chloro-2,3-dihydro-1-oxo-1H-indene-2-carboxylate feed was completed in 2.25 hours. After both feeds were complete, the reaction mixture was stirred for an additional 2 hours at 65° C., cooled to 10° C., and filtered. The isolated solid product of Formula Ia was washed with toluene (2×8 g) and then dried in vacuo at 45° C.

The filtrate from the previous reaction was evaporated in vacuo at 30° C. and diluted with toluene (about 7 g) to give a total weight of 20 g. This solution was charged with methyl 5-chloro-2,3-dihydro-1-oxo-1H-indene-2-carboxylate (2.25 g, 10 mmol) and toluene (6.65 g) and heated to 65° C., and the solutions of methyl 5-chloro-2,3-dihydro-1-oxo-1H-indene-2-carboxylate (20.21 g, 90 mmol, in 55.35 g of toluene) and tert-butyl hydroperoxide (12.88 g, 100 mmol) were co-fed as described before. After both feeds were complete, the reaction mixture was stirred for an additional 1.5 hours at 65° C., cooled to 10° C., and filtered. The isolated solid product of Formula Ia was washed and dried as before.

Using the filtrate from the previous run, the recycling process was repeated a second time as described in the previous paragraph except that 13.52 g (105 mmol) of tert-butyl hydroperoxide was used.

The recycling process was repeated a third time as before, except that 19.31 g (150 mmol) of tert-butyl hydroperoxide was used and the reaction mixture was held for 3 hours at 65° C. after both feeds were completed.

The results from these reactions, reported in the Table E12 below, were determined by HPLC analysis of both the isolated solids and the filtrates from each reaction. The overall reaction enantiomeric excess (ee) refers to the net enantiomeric excess of Ia produced during the run and is a weighted average of the enantiomeric excess of Ia in the solid and filtrate phases. The enantiomeric excess of the solid, isolated Ia may be higher than the reaction enantiomeric excess because the crystallization of Ia from the reaction mixture can enrich the solid with the predominant enantiomer.

TABLE E12

Results from Recycling Catalyst IIIb wherein $R^6$ is H

| Run | IIa Conversion (%) | Ia Isolated Weight (g) | Ia Isolated Yield (%)[a] | Isolated Ia ee (%)[b] | Reaction ee (%) |
|---|---|---|---|---|---|
| Initial | 83 | 17.52 | 73 | >98 | 95.1 |
| 1st Recycle | 86 | 19.89 | 82 | >98 | 92.3 |
| 2nd Recycle | 87 | 17.93 | 74 | 82.1 | 71.7 |
| 3rd Recycle | 91 | 24.05 | 99 | 62.6 | 62.9 |

[a]Yields based on IIa added to the reaction during that step.
[b]Enantiomeric excess (ee) positive values indicate an excess of the S enantiomer.

EXAMPLE 13

Preparation of methyl (2S)-5-chloro-2,3-dihydro-2-hydroxy-1-oxo-1H-indene-2-carboxylate (Formula Ia wherein $R^1$ is $OCH_3$ and $R^4$ is Cl) with recycle and makeup of catalyst A chiral zirconium complex was prepared by stirring zirconium(IV) acetylacetonate (0.73 g, 1.5 mmol) with IIIb wherein $R^6$ is H (1.61 g, 3.0 mmol) in toluene (4.7 g) for 40 minutes at 65° C. To the resulting solution was added methyl 5-chloro-2,3-dihydro-1-oxo-1H-indene-2-carboxylate (4.55 g, 20 mmol) and additional toluene (8.7 g). Two separate solutions of methyl 5-chloro-2,3-dihydro-1-oxo-1H-indene-2-carboxylate (18.38 g, 82 mmol in 54 g of toluene) and a 70% by weight solution of tert-butyl hydroperoxide in water (18.02 g, 140 mmol) were simultaneously co-fed to the reaction mixture while maintaining the reaction temperature at 65° C. The rates of addition were controlled so that the tert-butyl hydroperoxide feed was completed in 30 minutes and the methyl 5-chloro-2,3-dihydro-1-oxo-1H-indene-2-carboxylate feed was completed in 2.5 hours. After both feeds were complete, the reaction mixture was stirred for an additional 2 hours at 65° C., cooled to 10° C., and filtered. The resulting isolated solids of Ia were washed with toluene (2×8 g) and then dried in vacuo at 45° C. The filtrate (reaction filtrate and toluene wash) was washed with aqueous sodium bisulfite (pH adjusted to 8.8 with sodium carbonate), separated from the aqueous phase, and then concentrated in vacuo at 30° C. to provide a liquid weighing 10.4 g.

A catalyst makeup solution was prepared by heating IIIb wherein $R^6$ is H (1.07 g, 2 mmol) and zirconium(IV) acetylacetonate (0.195 g, 0.4 mmol) in toluene (2.73 g) at 50° C. for 1 hour. The concentrated filtrate from the previous run was charged with 1.0 g of the catalyst makeup solution (0.5 mmol IIIb wherein $R^6$ is H, 0.1 mmol zirconium(IV) acetylacetonate). After heating the mixture to 65° C., methyl 5-chloro-2,3-dihydro-1-oxo-1H-indene-2-carboxylate (2.29 g, 10 mmol) was added and then the solutions of methyl 5-chloro-2,3-dihydro-1-oxo-1H-indene-2-carboxylate (20.64 g, 92 mmol in 61 g of toluene) and tert-butyl hydroperoxide (18.02 g, 140 mmol) were co-fed as described before. After both feeds were complete, the reaction mixture was stirred for an additional 1 hour at 65° C. and cooled to 10° C. After adding water (10 mL) to the reaction mixture, it was filtered and the isolated solids dried as before. The filtrate was washed, separated, and concentrated as before to provide a liquid weighing 9.85 g.

Using the concentrated filtrate from the previous run, the recycling process (including catalyst makeup) was repeated a second time as described in the previous paragraph except the tert-butyl hydroperoxide was fed over 1.75 hours and the methyl 5-chloro-2,3-dihydro-1-oxo-1H-indene-2-carboxylate was fed over 3 hours. The solids and filtrate were treated as before. The filtrate was concentrated to provide a liquid weighing 10.77 g.

Using the concentrated filtrate from the previous run, the recycling process (including catalyst makeup) was repeated a third time as described in the previous paragraph except the tert-butyl hydroperoxide was fed over 2 hours. The solids and filtrate were treated as before.

The results from these reactions, reported in the Table E13 below, were determined by HPLC analysis of both the isolated solids of Ia and the filtrates from each reaction. The overall reaction enantiomeric excess (ee) refers to the net enantiomeric excess of Ia produced during the run and is a weighted average of the enantiomeric excess of Ia in the solid and filtrate phases. The enantiomeric excess of the solid, isolated Ia may be higher than the reaction enantiomeric excess because the crystallization of Ia from the reaction mixture can enrich the solid with the predominant enantiomer.

TABLE E13

Results from Recycling Catalyst IIIb wherein $R^6$ is H with Catalyst Makeup

| Run | IIa Conversion (%) | Ia Isolated Weight (g) | Ia Isolated Yield (%)[a] | Isolated Ia ee (%)[b] | Reaction ee (%) |
|---|---|---|---|---|---|
| Initial | 100 | 20.65 | 85.3 | 100 | 95.2 |
| 1st Recycle | 100 | 23.03 | 94.6 | 100 | 91.5 |
| 2nd Recycle | 99.6 | 22.45 | 92.1 | 98.6 | 85.6 |
| 3rd Recycle | 97.6 | 20.21 | 83.2 | 98.2 | 75.2 |

[a]Yields based on IIa added to the reaction during that step.
[b]Enantiomeric excess (ee) positive values indicate an excess of the S enantiomer.

EXAMPLE 14

Preparation of methyl (2S)-5-chloro-2,3-dihydro-2-hydroxy-1-oxo-1H-indene-2-carboxylate (Formula Ia wherein $R^1$ is $OCH_3$ and $R^4$ is Cl) using other ligands of Formulae III or IV The reaction conditions, reagents, and reagent amounts for the following examples are shown in Tables E14A and E14B. The conversion of IIa ($R^1$ is $OCH_3$, $R^4$ is Cl) and yield of Ia ($R^1$ is $OCH_3$, $R^4$ is Cl) are based on the amount of the limiting reagent IIa used in these reactions.

General procedure: A chiral zirconium complex was prepared by stirring either zirconium(IV) isopropoxide or zirconium(IV) acetylacetonate with a chiral ligand in toluene (1-2 mL) at 50° C. for 1 hour. The reaction mixture was evaporated to dryness in vacuo and then a toluene solution (2.00 mL) of methyl 5-chloro-2,3-dihydro-1-oxo-1H-indene-2-carboxylate (0.250 g/mL; 0.500 g, 2.23 mmol of methyl 5-chloro-2,3-dihydro-1-oxo-1H-indene-2-carboxylate) was added. The resulting reaction mixture was heated to the temperature indicated in Tables E14A and E14B, and then a 70% by weight solution of tert-butyl hydroperoxide in water (0.316 g, 0.340 mL, 2.46 mmol (1.10 equivalents) or 0.359 g, 0.386 mL, 2.79 mmol (1.25 equivalents)) was added. After the indicated time, the reaction mixture was diluted with acetonitrile (7.0 mL). The results of analysis by quantitative and chiral HPLC are shown in Tables E14A and E14B. $(R^6)_n$ specified in Tables E14A and E14B are the same on each phenyl ring.

TABLE E14A

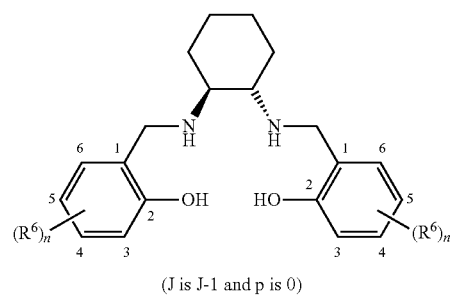

III (J is J-1 and p is 0)

Yield and ee (enantiomeric excess) of Ia ($R^1$ is $OCH_3$, $R^4$ is Cl) obtained with ligands of Formula III (J is J-1 and p is 0).

| $(R^6)_n$ | Ligand Equivalents[a] | Zr Complex Starting Material[b] | t-BuOOH Equivalents[a] | Temperature (° C.) | Time (h) | IIa Conversion (%) | Ia Yield (%) | Ia ee (%)[c] |
|---|---|---|---|---|---|---|---|---|
| H (n is 0) | 0.050 | Zr(OiPr)$_4$ | 1.10 | 30 | 20 | 95 | 76 | 0.5 |
| 3-tert-butyl | 0.080 | Zr(acac)$_4$ | 1.10 | 65 | 3.5 | 94 | 76 | 87.6 |
| 5-nitro | 0.050 | Zr(OiPr)$_4$ | 1.10 | 30 | 20 | 18 | 8 | 7.7 |
| 5-bromo | 0.050 | Zr(OiPr)$_4$ | 1.10 | 30 | 20 | 90 | 78 | −0.2 |
| 3-bromo-5-chloro | 0.050 | Zr(OiPr)$_4$ | 1.10 | 30 | 20 | 92 | 81 | −0.3 |
| 4,6-dichloro | 0.060 | Zr(acac)$_4$ | 1.10 | 65 | 3.5 | 92 | 72 | 0.0 |
| 3-methoxy | 0.060 | Zr(acac)$_4$ | 1.10 | 65 | 3.5 | 92 | 67 | −1.3 |
| 3-methoxy-5-bromo | 0.060 | Zr(acac)$_4$ | 1.10 | 65 | 3.5 | 91 | 73 | −0.9 |
| 3,5-dibromo | 0.060 | Zr(acac)$_4$ | 1.10 | 65 | 3.5 | 88 | 70 | 0.2 |
| 3,5-dichloro | 0.060 | Zr(acac)$_4$ | 1.10 | 65 | 3.5 | 90 | 73 | −0.5 |
| 3,4-dimethoxy | 0.060 | Zr(acac)$_4$ | 1.10 | 65 | 3.5 | 88 | 70 | −1.1 |
| 5-methoxy | 0.060 | Zr(acac)$_4$ | 1.10 | 65 | 3.5 | 94 | 72 | 1.1 |
| 3-tert-butyl-5-bromo | 0.048 | Zr(acac)$_4$ | 1.25 | 65 | 3.5 | 94 | 84 | 75 |

TABLE E14A-continued

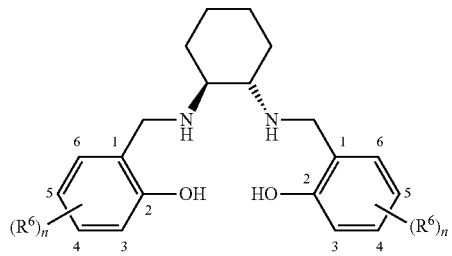

(J is J-1 and p is 0)

Yield and ee (enantiomeric excess) of Ia ($R^1$ is $OCH_3$, $R^4$ is Cl) obtained with ligands of Formula III (J is J-1 and p is 0).

| $(R^6)_n$ | Ligand Equivalents[a] | Zr Complex Starting Material[b] | t-BuOOH Equivalents[a] | Temperature (°C.) | Time (h) | IIa Conversion (%) | Ia Yield (%) | Ia ee (%)[c] |
|---|---|---|---|---|---|---|---|---|
| 3-tert-butyl-5-chloro | 0.048 | $Zr(acac)_4$ | 1.25 | 65 | 3.5 | 89 | 81 | 78 |
| 3-tert-butyl-5-methyl | 0.048 | $Zr(acac)_4$ | 1.25 | 65 | 3.5 | 97 | 85 | 71 |
| 3-tert-butyl-5-methoxy | 0.048 | $Zr(acac)_4$ | 1.25 | 65 | 3.5 | 98 | 73 | 64 |
| 3-tert-butyl-5-$O_2CC(CH_3)_3$ | 0.048 | $Zr(acac)_4$ | 1.25 | 65 | 3.5 | 95 | 87 | 49 |
| 3-tert-butyl-5-$OSi(iso-Pr)_3$ | 0.048 | $Zr(acac)_4$ | 1.25 | 65 | 3.5 | 95 | 85 | 71 |
| 3-tert-butyl-5-$O_2CC_6H_4(4'-OCH_3)$ | 0.048 | $Zr(acac)_4$ | 1.25 | 65 | 3.5 | 94 | 86 | 60 |
| 3-tert-butyl-5-$O_2CC_6H_4(4'-NO_2)$ | 0.048 | $Zr(acac)_4$ | 1.25 | 65 | 3.5 | 97 | 73 | 66 |
| 3-(1'-adamantyl)-5-methyl | 0.048 | $Zr(acac)_4$ | 1.25 | 65 | 3.5 | 95 | 86 | 36 |

[a]The number of equivalents relative to the amount of IIa used.
[b]0.04 equivalents of Zr complex starting material were used for all runs relative to the amount of IIa.
[c]Enantiomeric excess (ee) positive values indicate an excess of the S enantiomer; negative values indicate an excess of the R enantiomer.

TABLE E14B

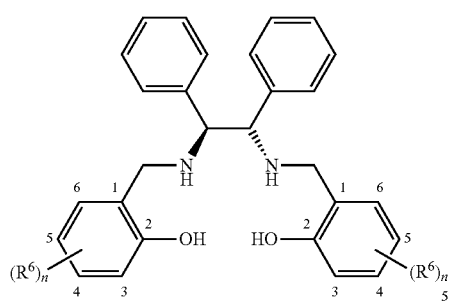

(J is J-5 and each q is 0)

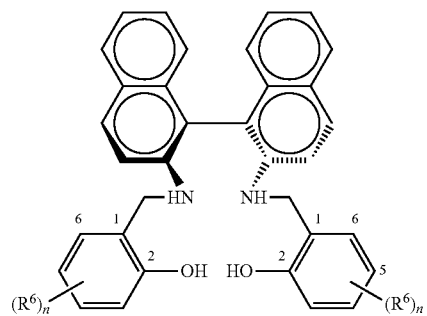

(J is J-9 and each q is 0)

TABLE E14B-continued

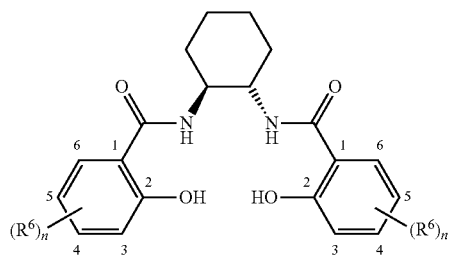

IVa

Yield and ee (enantiomeric excess) of Ia ($R^1$ is $OCH_3$, $R^4$ is Cl) obtained with ligands of Formula III (J is J-5 or J-9, each q is 0) and IVa

| $(R^6)_n$ | Ligand | Ligand Equivalents[a] | Zr Complex Starting Material | Zr Equivalents[a] | IIa Conversion (%) | Ia Yield (%) | Ia ee (%)[b] | Temperature (°C.) | Time (h) |
|---|---|---|---|---|---|---|---|---|---|
| 5-tert-butyl | III (J is J-5) | 0.08 | Zr(acac)$_4$ | 0.04 | 59 | 38 | 12.2 | 65 | 3.5 |
| 3,5-di-tert-butyl | III (J is J-5) | 0.08 | Zr(acac)$_4$ | 0.04 | 96 | 77 | 88.7 | 65 | 3.5 |
| 3,5-di-tert-butyl | III (J is J-9) | 0.08 | Zr(acac)$_4$ | 0.04 | 87 | 67 | 1.0 | 65 | 3.5 |
| 3,5-di-tert-butyl | IVa | 0.08 | Zr(acac)$_4$ | 0.04 | 92 | 71 | −6.7 | 65 | 3.5 |

[a]The number of equivalents relative to the amount of IIa used.
[b]Enantiomeric excess (ee) positive values indicate an excess of the S enantiomer; negative values indicate an excess of the R enantiomer.

By the procedures described herein together with methods known in the art, the ligands identified in Tables 1-3 and their zirconium complexes can be prepared. Table 4 illustrates examples of hydroxylated compounds of Formula I preparable from the corresponding β-dicarbonyl compounds of Formula II according to the process of the invention. The following abbreviations are used in the Tables which follow: "t" means tertiary, "s" means secondary, "n" means normal, "i" means iso, "c" means cyclo, "Me" means methyl, "Et" means ethyl, "Pr" means propyl, "i-Pr" means isopropyl, "Bu" means butyl, "Ph" means phenyl, "OMe" means methoxy, "OEt" means ethoxy, "SMe" means methylthio, "SEt" means ethylthio, "CN" means cyano, "NO$_2$" means nitro, "TMS" means trimethylsilyl, "S(O)Me" means methylsulfinyl, and "S(O)$_2$Me" means methylsulfonyl. For clarity, examples of compounds of Formula III (or their enantiomers) are illustrated in Tables 2A and 2B and examples of compounds of Formula IV (or their enantiomers) are illustrated in Tables 3A and 3B with the stereochemical relationship between J and the connecting nitrogen-containing linkages included in L specifically depicted as L-1 through L-12 shown in Table 1. The parts of Formula III or Formula IV or their enantiomers connected to the nitrogen-containing linkages of L are denoted $A^1$ and $A^2$.

TABLE 1

Illustrative Examples of L

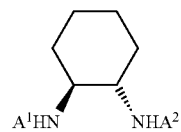

L-1

TABLE 1-continued

Illustrative Examples of L

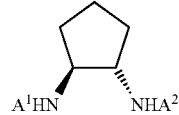

L-2

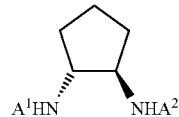

L-3

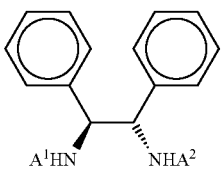

L-4

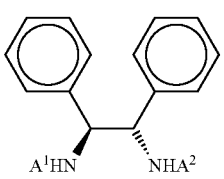

L-5

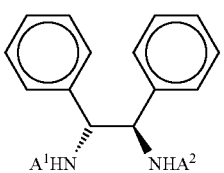

L-6

TABLE 1-continued

Illustrative Examples of L

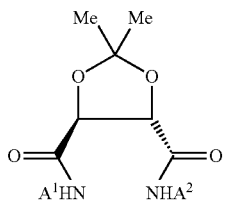
L-7

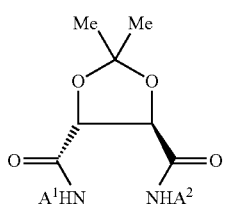
L-8

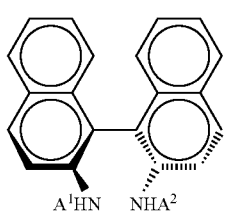
L-9

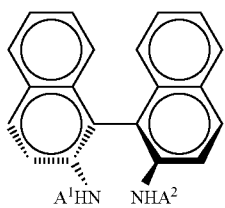
L-10

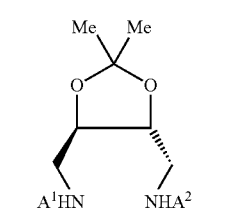
L-11

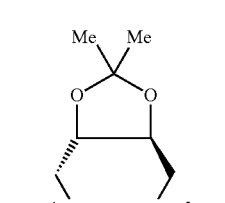
L12

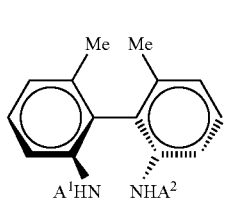
L-13

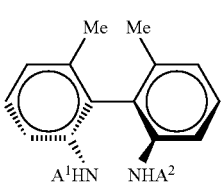
L-14

TABLE 2A

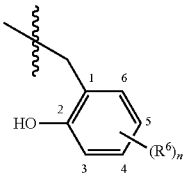

wherein $A^1$ and $A^2$ are both

| L | $(R^6)_n$ | |
|---|---|---|
| L-1 | 3,5-di-t-Bu | (IIIa, $R^6$ is $C(CH_3)_3$) |
| L-2 | 3,5-di-t-Bu | (ent-IIIa, $R^6$ is $C(CH_3)_3$) |
| L-1 | H | |
| L-2 | H | |
| L-1 | 3-t-Bu | (IIIa, $R^6$ is H) |
| L-2 | 3-t-Bu | (ent-IIIa, $R^6$ is H) |
| L-1 | 5-$NO_2$ | |
| L-2 | 5-$NO_2$ | |
| L-1 | 3-Br | |
| L-2 | 3-Br | |
| L-1 | 3-Br, 5-Cl | |
| L-2 | 3-Br, 5-Cl | |
| L-1 | 3-t-Bu, 5-Cl | |
| L-2 | 3-t-Bu, 5-Cl | |
| L-1 | 3-t-Bu, 5-Br | |
| L-2 | 3-t-Bu, 5-Br | |
| L-1 | 3-t-Bu, 5-Me | |
| L-2 | 3-t-Bu, 5-Me | |
| L-1 | 3-t-Bu, 5-OSi(i-Pr)$_3$ | |
| L-2 | 3-t-Bu, 5-OSi(i-Pr)$_3$ | |
| L-1 | 3-t-Bu, 5-OMe | |
| L-2 | 3-t-Bu, 5-OMe | |
| L-1 | 3,5-di-Me | |
| L-2 | 3,5-di-Me | |
| L-1 | 3,5-di-TMS | |
| L-2 | 3,5-di-TMS | |
| L-1 | 3,5-di-Cl | |
| L-2 | 3,5-di-Cl | |
| L-3 | 3,5-di-t-Bu | |
| L-4 | 3,5-di-t-Bu | |
| L-3 | H | |
| L-4 | H | |
| L-3 | 3,5-di-Me | |
| L-4 | 3,5-di-Me | |
| L-3 | 3,5-di-TMS | |
| L-4 | 3,5-di-TMS | |
| L-3 | 3,5-di-Cl | |
| L-4 | 3,5-di-Cl | |
| L-5 | 3,5-di-t-Bu | (IIIb, $R^6$ is $C(CH_3)_3$) |
| L-6 | 3,5-di-t-Bu | (ent-IIIb, $R^6$ is $C(CH_3)_3$) |
| L-5 | H | |
| L-6 | H | |
| L-5 | 3,5-di-Me | |
| L-6 | 3,5-di-Me | |
| L-5 | 3,5-di-TMS | |

TABLE 2A-continued

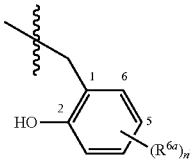

wherein A¹ and A² are both

| L | $(R^6)_n$ |
|---|---|
| L-6 | 3,5-di-TMS |
| L-5 | 3-t-Bu, 5-Me |
| L-6 | 3-t-Bu, 5-Me |
| L-7 | 3,5-di-t-Bu |
| L-8 | 3,5-di-t-Bu |
| L-7 | H |
| L-8 | H |
| L-7 | 3,5-di-Me |
| L-8 | 3,5-di-Me |
| L-7 | 3,5-di-TMS |
| L-8 | 3,5-di-TMS |
| L-7 | 3,5-di-Cl |
| L-8 | 3,5-di-Cl |
| L-9 | 3,5-di-t-Bu |
| L-10 | 3,5-di-t-Bu |
| L-9 | H |
| L-10 | H |
| L-9 | 3,5-di-Me |
| L-10 | 3,5-di-Me |
| L-9 | 3,5-di-TMS |
| L-10 | 3,5-di-TMS |
| L-9 | 3,5-di-Cl |
| L-10 | 3,5-di-Cl |
| L-11 | 3,5-di-TMS |
| L-12 | 3,5-di-TMS |
| L-11 | H |
| L-12 | H |
| L-11 | 3,5-di-Me |
| L-12 | 3,5-di-Me |
| L-11 | 3,5-di-TMS |
| L-12 | 3,5-di-TMS |
| L-11 | 3,5-di-Cl |
| L-12 | 3,5-di-Cl |
| L-13 | 3,5-di-t-Bu |
| L-14 | 3,5-di-t-Bu |
| L-13 | H |
| L-14 | H |
| L-13 | 3,5-di-Me |
| L-14 | 3,5-di-Me |
| L-13 | 3,5-di-TMS |
| L-14 | 3,5-di-TMS |
| L-13 | 3,5-di-Cl |
| L-14 | 3,5-di-Cl |
| L-5 | 3,5-di-Cl |
| L-6 | 3,5-di-Cl |
| L-5 | 3-t-Bu (IIIb, $R^6$ is H) |
| L-6 | 3-t-Bu (ent-IIIb, $R^6$ is H) |
| L-1 | 3-t-Bu, 5-Me |
| L-2 | 3-t-Bu, 5-Me |

TABLE 2B

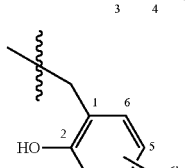

wherein A¹ is and A² is

| L | $(R^{6a})_na$ | $(R^{6b})_nb$ |
|---|---|---|
| L-1 | 3,5-di-t-Bu | 3-t-Bu |
| L-2 | 3,5-di-t-Bu | 3-t-Bu |
| L-5 | 3-t-Bu | 3,5-di-t-Bu |
| L-6 | 3-t-Bu | 3,5-di-t-Bu |
| L-1 | 3,5-di-TMS | 3-t-Bu |
| L-2 | 3,5-di-TMS | 3-t-Bu |
| L-5 | 3,5-di-TMS | 3-t-Bu |
| L-6 | 3,5-di-TMS | 3-t-Bu |

TABLE 3A wherein A¹ and A² are both

| L | $(R^6)_n$ |
|---|---|
| L-1 | 3,5-di-t-Bu |
| L-2 | 3,5-di-t-Bu |
| L-1 | H |
| L-2 | H |
| L-1 | 3-t-Bu |
| L-2 | 3-t-Bu |
| L-1 | 5-NO$_2$ |
| L-2 | 5-NO$_2$ |
| L-1 | 3-Br |
| L-2 | 3-Br |
| L-1 | 3-Br, 5-Cl |
| L-2 | 3-Br, 5-Cl |
| L-1 | 3-t-Bu, 5-Cl |
| L-2 | 3-t-Bu, 5-Cl |
| L-1 | 3-t-Bu, 5-Br |
| L-2 | 3-t-Bu, 5-Br |
| L-1 | 3-t-Bu, 5-Me |
| L-2 | 3-t-Bu, 5-Me |
| L-1 | 3-t-Bu, 5-OSi(i-Pr)$_3$ |
| L-2 | 3-t-Bu, 5-OSi(i-Pr)$_3$ |
| L-1 | 3-t-Bu, 5-OMe |
| L-2 | 3-t-Bu, 5-OMe |
| L-1 | 3,5-di-Me |
| L-2 | 3,5-di-Me |
| L-1 | 3,5-di-TMS |
| L-2 | 3,5-di-TMS |
| L-1 | 3,5-di-Cl |
| L-2 | 3,5-di-Cl |
| L-3 | 3,5-di-t-Bu |
| L-4 | 3,5-di-t-Bu |
| L-3 | H |

TABLE 3A-continued

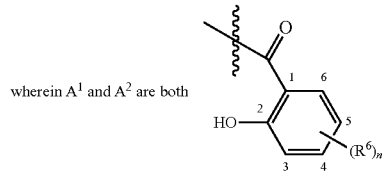

wherein $A^1$ and $A^2$ are both

| L | $(R^6)_n$ |
|---|---|
| L-4 | H |
| L-3 | 3,5-di-Me |
| L-4 | 3,5-di-Me |
| L-3 | 3,5-di-TMS |
| L-4 | 3,5-di-TMS |
| L-3 | 3,5-di-Cl |
| L-4 | 3,5-di-Cl |
| L-5 | 3,5-di-t-Bu |
| L-6 | 3,5-di-t-Bu |
| L-5 | H |
| L-6 | H |
| L-5 | 3,5-di-Me |
| L-8 | 3,5-di-Me |
| L-7 | 3,5-di-TMS |
| L-8 | 3,5-di-TMS |
| L-7 | 3,5-di-Cl |
| L-8 | 3,5-di-Cl |
| L-9 | 3,5-di-t-Bu |
| L-10 | 3,5-di-t-Bu |
| L-9 | H |
| L-10 | H |
| L-9 | 3,5-di-Me |
| L-10 | 3,5-di-Me |
| L-6 | 3,5-di-Me |
| L-5 | 3,5-di-TMS |
| L-6 | 3,5-di-TMS |
| L-9 | 3,5-di-TMS |
| L-10 | 3,5-di-TMS |
| L-9 | 3,5-di-Cl |
| L-10 | 3,5-di-Cl |
| L-11 | 3,5-di-t-Bu |
| L-12 | 3,5-di-t-Bu |
| L-11 | H |
| L-12 | H |
| L-11 | 3,5-di-Me |
| L-12 | 3,5-di-Me |
| L-11 | 3,5-di-TMS |
| L-12 | 3,5-di-TMS |
| L-11 | 3,5-di-Cl |
| L-12 | 3,5-di-Cl |
| L-13 | 3,5-di-t-Bu |
| L-14 | 3,5-di-t-Bu |
| L-13 | H |
| L-14 | H |
| L-13 | 3,5-di-Me |

TABLE 3A-continued

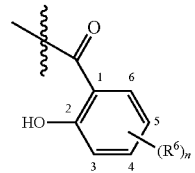

wherein $A^1$ and $A^2$ are both

| L | $(R^6)_n$ |
|---|---|
| L-14 | 3,5-di-Me |
| L-13 | 3,5-di-TMS |
| L-14 | 3,5-di-TMS |
| L-13 | 3,5-di-Cl |
| L-14 | 3,5-di-Cl |
| L-5 | 3-t-Bu |
| L-6 | 3-t-Bu |
| L-5 | 3,5-di-Cl |
| L-6 | 3,5-di-Cl |

TABLE 3B

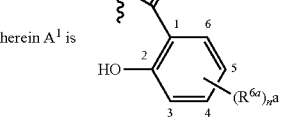

wherein $A^1$ is

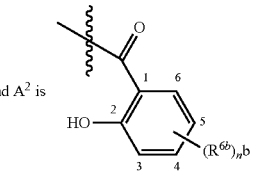

and $A^2$ is

| L | $(R^{6a})_n$a | $(R^{6b})_n$b |
|---|---|---|
| L-1 | 3,5-di-t-Bu | 3-t-Bu |
| L-2 | 3,5-di-t-Bu | 3-t-Bu |
| L-5 | 3-t-Bu | 3,5-di-t-Bu |
| L-6 | 3-t-Bu | 3,5-di-t-Bu |
| L-1 | 3,5-di-TMS | 3-t-Bu |
| L-2 | 3,5-di-TMS | 3-t-Bu |
| L-5 | 3,5-di-TMS | 3-t-Bu |
| L-6 | 3,5-di-TMS | 3-t-Bu |

TABLE 4

Illustrative examples of hydroxylated compounds of Formula I preparable from the corresponding β-dicarbonyl compounds of Formula II according to the process of the invention.

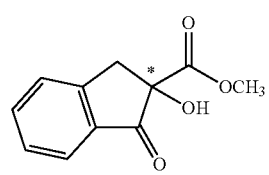

TABLE 4-continued
Illustrative examples of hydroxylated compounds of Formula I preparable from the corresponding β-dicarbonyl compounds of Formula II according to the process of the invention.
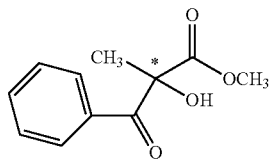
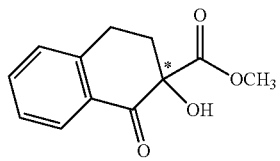
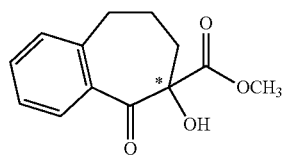
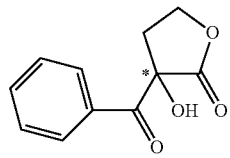
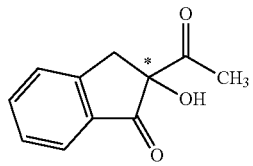
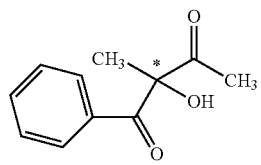
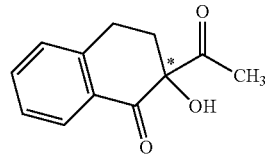
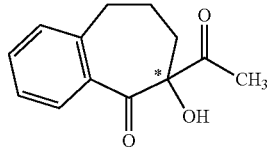
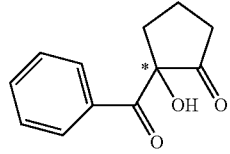

TABLE 4-continued
Illustrative examples of hydroxylated compounds of Formula I preparable from the corresponding β-dicarbonyl compounds of Formula II according to the process of the invention.
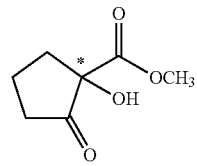
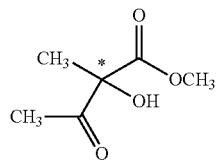
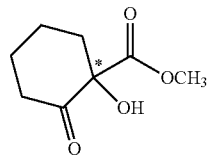
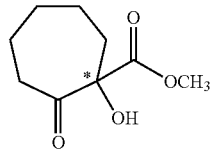
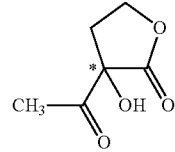
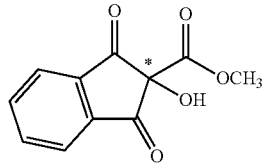
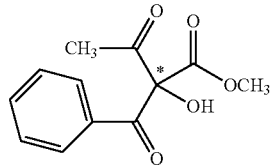
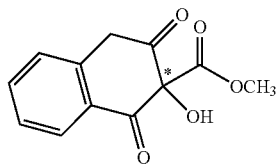
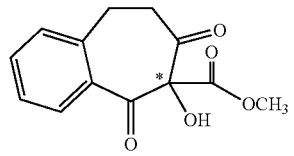

TABLE 4-continued
Illustrative examples of hydroxylated compounds of Formula I preparable from the corresponding β-dicarbonyl compounds of Formula II according to the process of the invention.
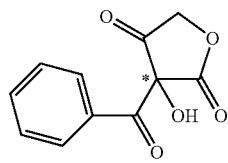
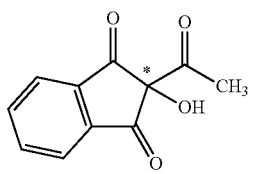
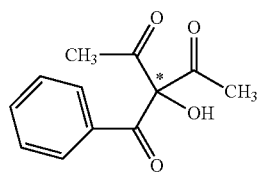
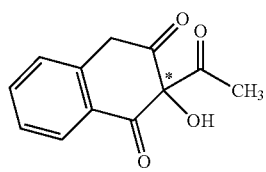
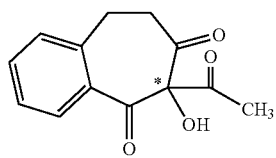
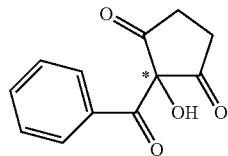
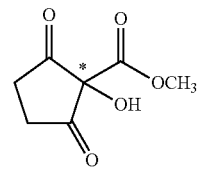
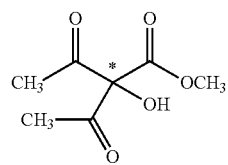

TABLE 4-continued
Illustrative examples of hydroxylated compounds of Formula I preparable from the corresponding β-dicarbonyl compounds of Formula II according to the process of the invention.
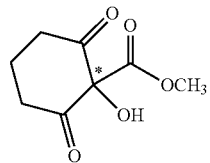
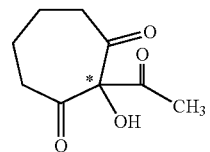
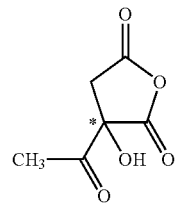
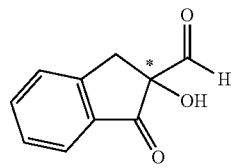
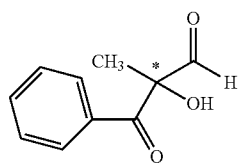
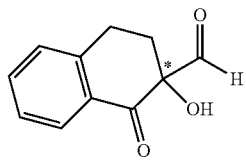
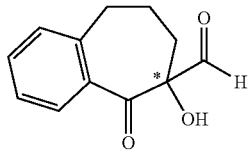
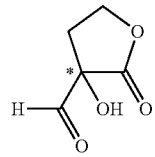

TABLE 4-continued
Illustrative examples of hydroxylated compounds of Formula I preparable from the corresponding β-dicarbonyl compounds of Formula II according to the process of the invention.
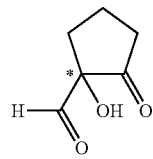
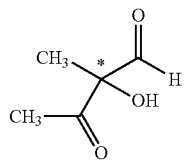
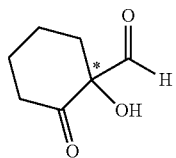
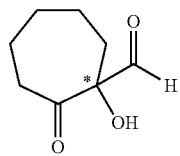
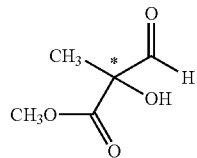
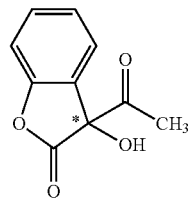
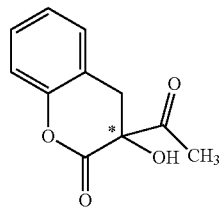
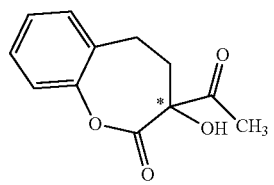

TABLE 4-continued
Illustrative examples of hydroxylated compounds of Formula I preparable from the corresponding β-dicarbonyl compounds of Formula II according to the process of the invention.
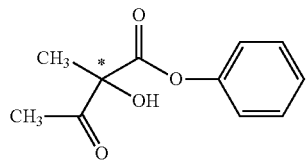
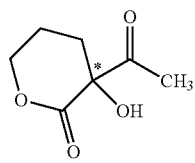
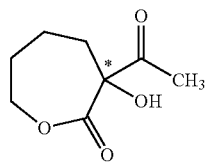
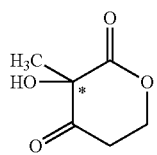
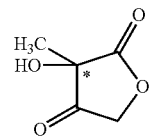
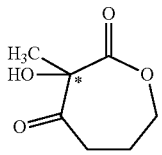
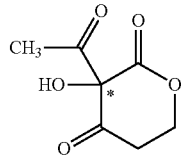
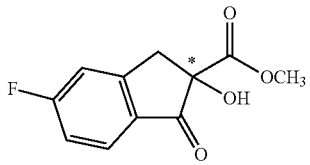
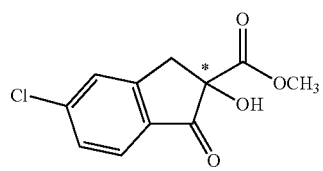

TABLE 4-continued
Illustrative examples of hydroxylated compounds of Formula I preparable from the corresponding β-dicarbonyl compounds of Formula II according to the process of the invention.
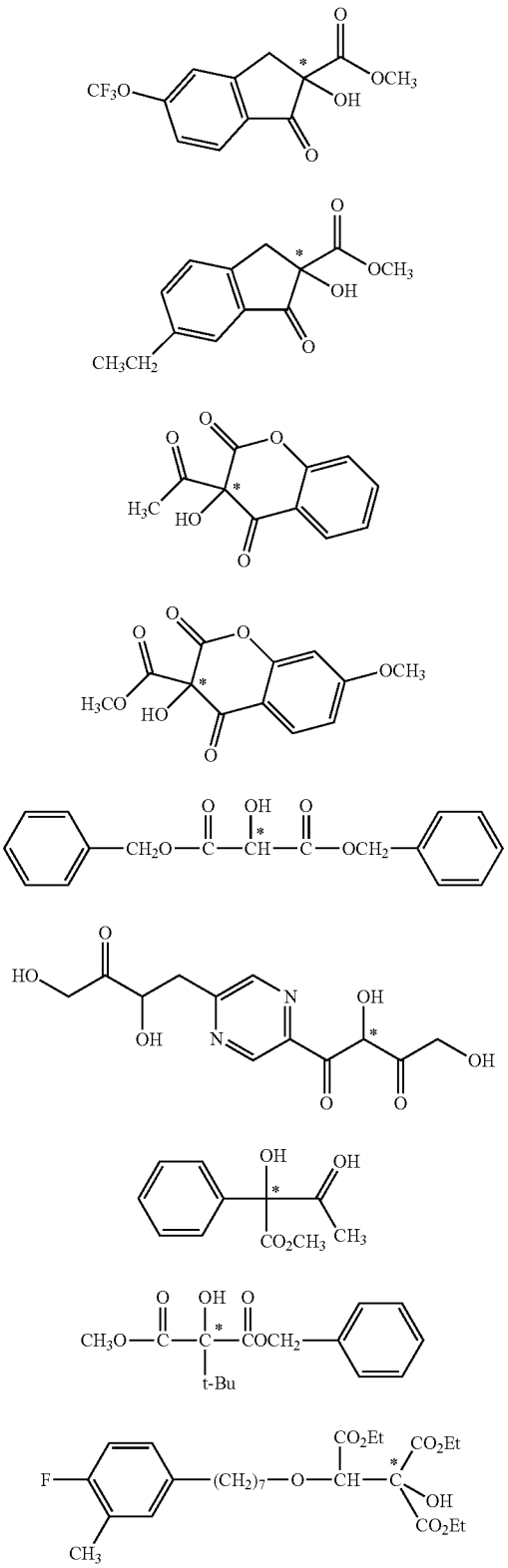

TABLE 4-continued

Illustrative examples of hydroxylated compounds of Formula I preparable from the corresponding β-dicarbonyl compounds of Formula II according to the process of the invention.

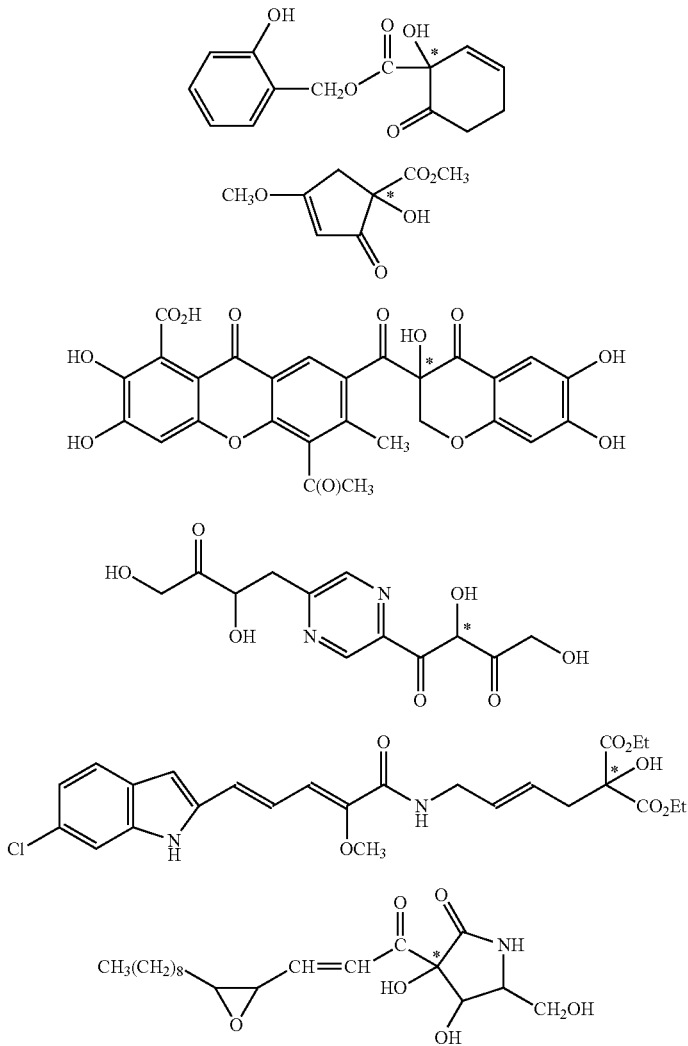

(* indicates a hydroxylation center comprising the hydroxy group introduced by the process of the invention. When a molecule does not have a mirror plane of symmetry through the hydroxylation center, the hydroxylation center is a chiral center.)

The invention claimed is:

1. A chiral compound of Formula III of at least about 50% enantiomeric purity

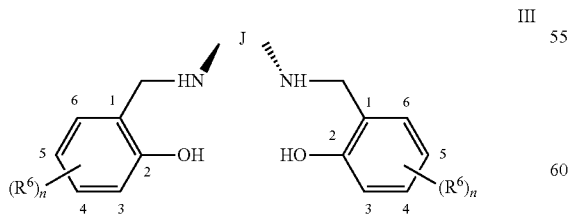

III wherein

J is a linking chain of 2 members consisting of carbon atom members; the linking chain fused through adjacent linking chain members to a cyclohexyl ring optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; such that the attached nitrogen atoms are held in a stereospecific orientation with respect to J and each other as depicted;

each $R^6$ is independently selected from the group consisting of halogen; $NO_2$; cyano; $C_2$-$C_5$ alkoxycarbonyl; $N(C_1$-$C_4$ alkyl$)_2$; $CON(C_1$-$C_4$ alkyl$)_2$; $C_1$-$C_4$ alkoxy; $C_2$-$C_5$ alkylcarbonyloxy; $C_2$-$C_5$ alkoxycarbonyloxy; phenylcarbonyloxy optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; tri($C_1$-$C_4$ alkyl)silyl; tri($C_1$-$C_4$ alkyl)siloxy; $C_1$-$C_4$ alkyl optionally substituted with 1-3 phenyl rings; $C_3$-$C_6$ cycloalkyl optionally substituted with $C_1$-$C_2$ alkyl; adamantyl; a phenyl ring, or a 5- or 6-membered heteroaromatic ring, each ring optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; and when two $R^6$ are attached to adjacent phenyl ring carbon atoms, said two $R^6$ may be taken together with the phenyl ring to form a naphthalene ring system optionally substituted on either ring of said naphthalene ring system with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; and each n is independently an integer from 0 to 4;

provided that (a) when J is a $C_6$ cycloalkyl ring connected via adjacent carbon atoms to the remainder of Formula III, then at least one n is an integer from 1 to 4; and (b) when J is a $C_6$ cycloalkyl ring connected via adjacent carbon atoms to the remainder of Formula III, on one phenyl ring n is 2 and $(R^6)_n$ is 3-t-butyl-5-methyl, then $(R^6)_n$ on the other phenyl ring is other than 3-t-butyl-5-methyl.

2. The chiral compound of claim 1 that is Formula IIIa

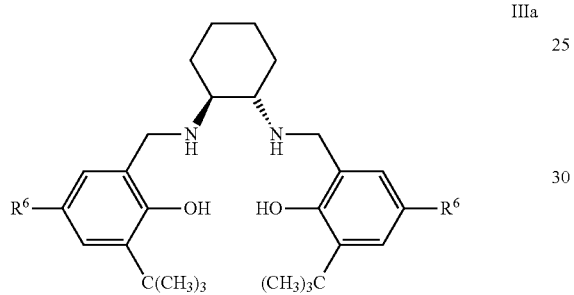

IIIa wherein each $R^6$ is the same and is selected from H and $C(CH_3)_3$.

3. A chiral compound of Formula ent-III of at least about 50% enantiomeric purity

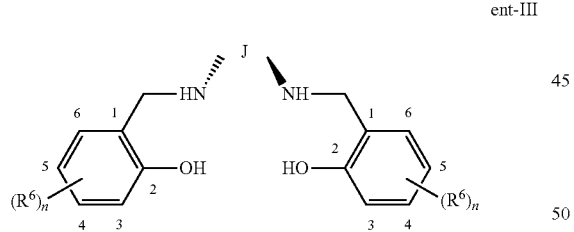

ent-III wherein
J is a linking chain of 2 members consisting of carbon atom members; the linking chain fused through adjacent linking chain members to a cyclohexyl ring optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; such that the attached nitrogen atoms are held in a stereospecific orientation with respect to J and each other as depicted;

each $R^6$ is independently selected from the group consisting of halogen; $NO_2$; cyano; $C_2$-$C_5$ alkoxycarbonyl; $N(C_1$-$C_4$ alkyl$)_2$; $CON(C_1$-$C_4$ alkyl$)_2$; $C_1$-$C_4$ alkoxy; $C_2$-$C_5$ alkylcarbonyloxy; $C_2$-$C_5$ alkoxycarbonyloxy; phenylcarbonyloxy optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; tri($C_1$-$C_4$ alkyl)silyl; tri($C_1$-$C_4$ alkyl)siloxy; $C_1$-$C_4$ alkyl optionally substituted with 1-3 phenyl rings; $C_3$-$C_6$ cycloalkyl optionally substituted with $C_1$-$C_2$ alkyl; adamantyl; a phenyl ring, or a 5- or 6-membered heteroaromatic ring, each ring optionally substituted with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; and when two $R^6$ are attached to adjacent phenyl ring carbon atoms, said two $R^6$ may be taken together with the phenyl ring to form a naphthalene ring system optionally substituted on either ring of said naphthalene ring system with substituents independently selected from $C_1$-$C_4$ alkyl, $C_1$-$C_4$ haloalkyl, $C_1$-$C_4$ alkoxy, $C_1$-$C_4$ haloalkoxy, halogen and nitro; and each n is independently an integer from 0 to 4;

provided that (a) when J is a $C_6$ cycloalkyl ring connected via adjacent carbon atoms to the remainder of Formula ent-III, then at least one n is an integer from 1 to 4; (b) when J is a $C_6$ cycloalkyl ring connected via adjacent carbon atoms to the remainder of Formula ent-III, on one phenyl ring n is 2 and $(R^6)_n$ is 3-t-butyl-5-methyl, then $(R^6)_n$ on the other phenyl ring is other than 3-t-butyl-5-methyl; and (c) when J is a $C_6$ cycloalkyl ring connected via adjacent carbon atoms to the remainder of Formula ent-III, on one phenyl ring n is 2 and $(R^6)_n$ is 3-t-butyl-5-t-butyl, then $(R^6)_n$ on the other phenyl ring is other than 3-t-butyl-5-t-butyl.

4. The chiral compound of claim 3 that is Formula ent-IIIa

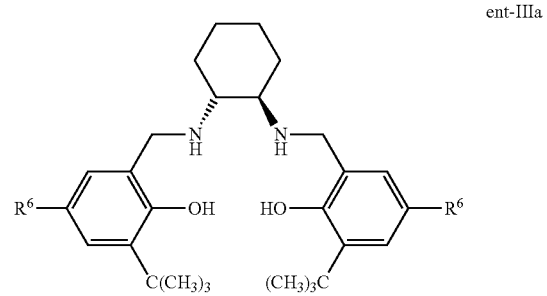

ent-IIIa wherein $R^6$ is H.

5. The chiral compound of claim 2 that is 2,2'-[(1S,2S)-1,2-cyclohexanediylbis(iminomethylene)]bis[4,6-bis(1,1-dimethylethyl)phenol].

6. The chiral compound of claim 2 that is 2,2'-[(1S,2S)-1,2-cyclohexanediylbis(iminomethylene)]bis[6-(1,1-dimethylethyl)phenol].

7. A chiral compound of claim 1 wherein
J is

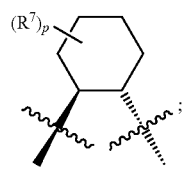

each $R^7$ is independently selected from $C_1$-$C_4$ alkyl, $C_1$-$C_4$ alkoxy and halogen; and
p is an integer from 0 to 4.

8. A chiral compound of claim 3 wherein J is
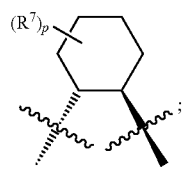
each $R^7$ is independently selected from $C_1$-$C_4$ alkyl, $C_1$-$C_4$ alkoxy and halogen; and
p is an integer from 0 to 4.
* * * * *